US012672766B2

(12) United States Patent
Kitamura et al.

(10) Patent No.: US 12,672,766 B2
(45) Date of Patent: Jul. 7, 2026

(54) RECORDING MEDIUM, METHOD FOR GENERATING LEARNING MODEL, IMAGE PROCESSING DEVICE, AND SURGICAL OPERATION ASSISTING SYSTEM

(71) Applicant: Anaut Inc., Yokohama (JP)

(72) Inventors: Naoki Kitamura, Tokyo (JP); Yuta Kumazu, Yokohama (JP); Nao Kobayashi, Tokyo (JP)

(73) Assignee: Anaut Inc., Yokohama (JP)

( * ) Notice: Subject to any disclaimer, the term of this patent is extended or adjusted under 35 U.S.C. 154(b) by 500 days.

(21) Appl. No.: 17/795,408

(22) PCT Filed: Feb. 1, 2021

(86) PCT No.: PCT/JP2021/003489
§ 371 (c)(1),
(2) Date: Jul. 26, 2022

(87) PCT Pub. No.: WO2021/153797
PCT Pub. Date: Aug. 5, 2021

(65) Prior Publication Data
US 2023/0098859 A1     Mar. 30, 2023

(30) Foreign Application Priority Data

Jan. 30, 2020     (WO) .................. PCT/JP2020/003481

(51) Int. Cl.
*A61B 1/04*          (2006.01)
*A61B 1/00*          (2006.01)
*A61B 34/00*         (2016.01)
(52) U.S. Cl.
CPC .......... *A61B 1/04* (2013.01); *A61B 1/000094* (2022.02); *A61B 1/000096* (2022.02); *A61B 34/00* (2016.02)

(58) Field of Classification Search
CPC .......... A61B 1/00009; A61B 1/000094; A61B 1/000095; A61B 1/000096; A61B 1/04;
(Continued)

(56) References Cited

U.S. PATENT DOCUMENTS

2008/0123927 A1     5/2008  Miga et al.
2010/0169815 A1     7/2010  Zhao et al.
(Continued)

FOREIGN PATENT DOCUMENTS

CN          103908344 A     7/2014
CN          105534606 A     5/2016
(Continued)

OTHER PUBLICATIONS

English translation of International Search Report of PCT/JP2021/003489, mailed Apr. 13, 2021, 3 pages.
(Continued)

*Primary Examiner* — Ryan N Henderson
(74) *Attorney, Agent, or Firm* — Christian S. Hans; Bret E. Field; Bozicevic, Field & Francis LLP

(57) ABSTRACT

A non-transitory recording medium recoding a program that causes a computer to execute processing includes: acquiring an operation field image obtained by imaging an operation field of an endoscopic surgery; inputting the acquired operation field image to a learning model trained to output information on a connective tissue between a preservation organ and a resection organ in a case where the operation field image is input, and acquiring information on the connective tissue included in the operation field image; and outputting navigation information when treating the connective tissue between the preservation organ and the resection organ on the basis of the information acquired from the learning model.

12 Claims, 35 Drawing Sheets

(58) Field of Classification Search
CPC ........... A61B 5/00; A61B 34/00; A61B 34/10;
A61B 2034/101; A61B 2034/102; A61B
2034/104; A61B 2034/105; A61B
2034/107; A61B 2034/108
See application file for complete search history.

(56) References Cited

U.S. PATENT DOCUMENTS

| 2012/0004557 | A1 | 1/2012 | McDowall et al. | |
|---|---|---|---|---|
| 2014/0343586 | A1 | 11/2014 | Sakuragi | |
| 2018/0078313 | A1 | 3/2018 | Comaniciu et al. | |
| 2018/0296280 | A1 | 10/2018 | Kurihara et al. | |
| 2018/0353244 | A1* | 12/2018 | Kashima | A61B 18/00 |
| 2019/0262084 | A1 | 8/2019 | Roh et al. | |
| 2019/0285638 | A1 | 9/2019 | Mizoguchi et al. | |
| 2020/0193236 | A1 | 6/2020 | Oosake | |
| 2020/0297422 | A1 | 9/2020 | Gocho et al. | |
| 2021/0015343 | A1 | 1/2021 | Uyama et al. | |
| 2021/0287395 | A1 | 9/2021 | Ishikake et al. | |
| 2021/0307841 | A1* | 10/2021 | Buch | A61B 5/749 |

FOREIGN PATENT DOCUMENTS

| CN | 109893240 | A | 6/2019 |
|---|---|---|---|
| JP | 2013-154037 | A | 8/2013 |
| JP | 2013-531538 | A | 8/2013 |
| JP | 2019-97661 | A | 6/2019 |
| JP | 2019-162339 | A | 9/2019 |
| KR | 10-2015-0113929 | A | 10/2015 |
| WO | WO2017109912 | A1 | 6/2017 |
| WO | WO2017200066 | A1 | 11/2017 |
| WO | WO2019054045 | A1 | 3/2019 |
| WO | WO2019097804 | A1 | 5/2019 |
| WO | WO2019116593 | A1 | 6/2019 |
| WO | WO2019246580 | A1 | 12/2019 |
| WO | WO2020110278 | A1 | 6/2020 |

OTHER PUBLICATIONS

Shinohara et al., WS15-2, Microanatomical structure recognition by image segmentation; visualization of loose connective tissue gaps in robot-assisted gastric cancer surgery, Abstracts of the 75th Annual Meeting of the Japanese Society of Gastroenterological Surgery, Japan, The Japanese Society of Gastroenterological Surgery, Dec. 2020, p. 134, and its machine translation, 2 pages.
First Office Action for Chinese Application No. 202180011878.3 mailed Mar. 28, 2025, with its English translation, 15 pages.

* cited by examiner

S421 ACQUIRE IMAGE

S422 RECOGNIZE ORGAN, CONNECTIVE TISSUE FROM IMAGE

S423 CALCULATE SCORE FROM A FEATURE OF IMAGE OF TISSUE AND MODEL

S424 SUPERIMPOSE SCORE

FIG. 14

INPUT IMAGE

OUTPUT IMAGE

DEVELOP TARGET REGION AND REMOVE LOOSENESS!
( LIFT ADIPOSE TISSUE!)

DEVELOP TARGET REGION AND REMOVE LOOSENESS!
( EXPAND ADIPOSE TISSUE TO THE LEFT AND RIGHT! )

NO MORE LOOSENESS IN TARGET REGION.
RESECTABLE.

450

PREDICTION IMAGE

OPERATION FIELD IMAGE

RECORDING MEDIUM, METHOD FOR GENERATING LEARNING MODEL, IMAGE PROCESSING DEVICE, AND SURGICAL OPERATION ASSISTING SYSTEM

CROSS-REFERENCE TO RELATED APPLICATIONS

This application is the national phase of PCT International Application No. PCT/JP2021/003489 which has an International filing date of Feb. 1, 2021 and designated the United States of America.

FIELD

The present invention relates to a computer program, a method for generating a learning model, an image processing device, and a surgical operation assisting system.

BACKGROUND

An endoscopic surgical operation, in which a surgical operation is performed by opening a plurality of small holes of approximately 3 to 10 mm in a living body to reach an abdominal cavity or a thoracic cavity, and by inserting an endoscope or a surgical operation instrument through the holes without making an incision in the living body, has been performed.

As a technology of executing the endoscopic surgical operation, a surgical operation system capable of performing a surgical treatment by operating the surgical operation instrument with a medical manipulator while viewing an image acquired by the endoscope with a display has been suggested (for example, refer to Japanese Patent Application Laid-Open No. 2013-531538).

In a surgical operation, it is important to develop a target organ into a state suitable for treatment while performing the treatment. However, in an endoscopic surgery, it is difficult to grasp a whole image of the organ, and since it is lack of a tactile sensation, it is difficult to determine that an optimal state for the treatment will be obtained when the organ is tracked in which direction and how much.

SUMMARY

The invention has been made in consideration of such circumstances, and an object thereof is to provide a technology capable of easily grasping a state of a surgical operation target.

To accomplish the object, according to a main aspect of the invention, a computer is caused to execute processes of: acquiring an operation field image obtained by imaging an operation field of an endoscopic surgery; inputting the acquired operation field image to a learning model trained to output information on a connective tissue between a preservation organ and a resection organ in a case where the operation field image is input, and acquiring information on the connective tissue included in the operation field image; and outputting navigation information when treating the connective tissue between the preservation organ and the resection organ on the basis of the information acquired from the learning model.

According to the invention, it is possible to easily graph a state of a surgical operation target.

The above and further objects and features of the invention will more fully be apparent from the following detailed description with accompanying drawings.

FIG. 14 is a schematic view illustrating a configuration example of a learning model;

FIG. 25 is a schematic view describing a configuration of a learning model according to Embodiment 5;

DESCRIPTION OF EMBODIMENTS

Figure 1:
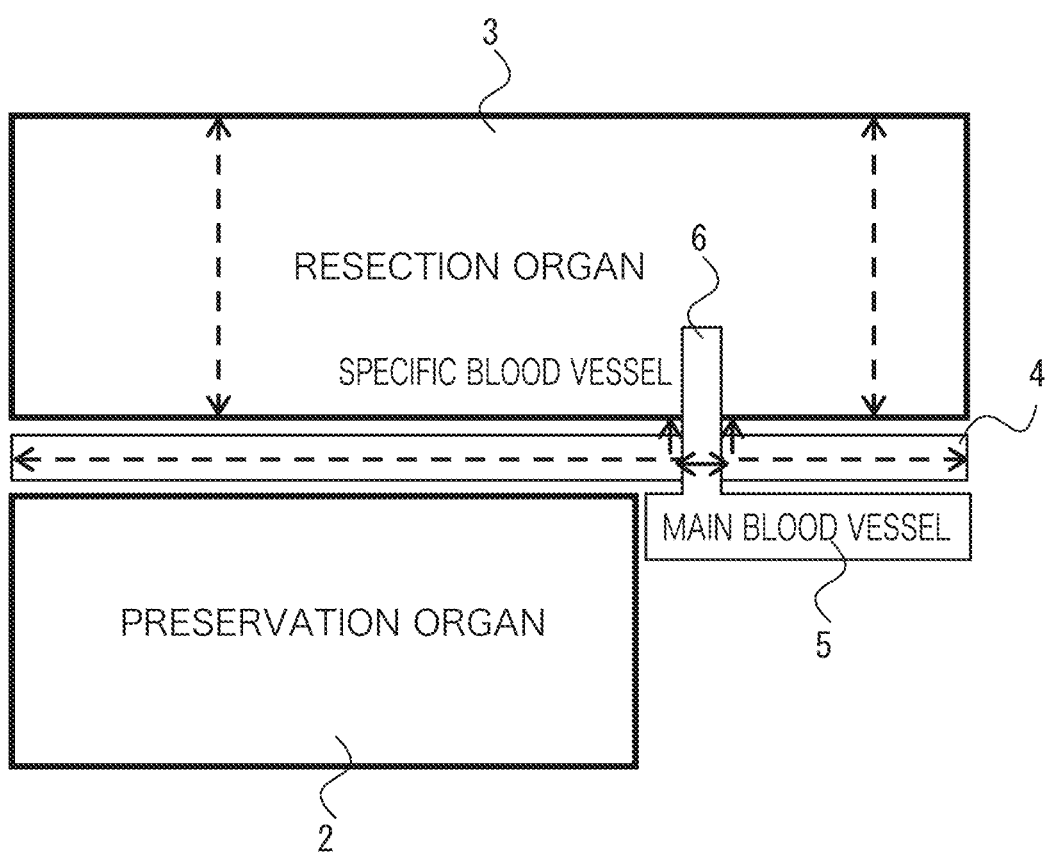
FIG. 1 is a view describing a surgical operation using a surgical operation assisting system of an embodiment.

The contents of embodiments of the invention will be described in a list. For example, the invention has the following configurations.

[Item 1]

A surgical operation assisting system, including:

an anatomical state acquisition unit configured to acquire information indicating an anatomical state in the surgical operation;

a score calculation unit configured to determine a score of the anatomical state on the basis of the information; and a score output unit configured to output information based on the score.

[Item 2]

The surgical operation assisting system according to Item 1, wherein the anatomical state includes a relationship between a plurality of organs.

[Item 3]

The surgical operation assisting system according to Item 1 or 2, wherein the anatomical state represents the degree of a state suitable for treatment on a surgical operation target.

[Item 4]

The surgical operation assisting system according to any one of Items 1 to 3, wherein the information includes at least a captured image of an operation field.

[Item 5]

The surgical operation assisting system according to Item 4, wherein the image includes at least any one among a visible image, an infrared image, and a depth map.

[Item 6]

The surgical operation assisting system according to any one of Items 1 to 5, wherein the score calculation unit determines the score in correspondence with the magnitude of an area of a surgical operation target.

[Item 7]

The surgical operation assisting system according to any one of Items 1 to 5, wherein the score calculation unit determines the score in correspondence with the degree of deformation of a surgical operation target.

[Item 8]

The surgical operation assisting system according to any one of Items 1 to 5, wherein the score calculation unit determines the score in correspondence with information including a color of a surgical operation target.

[Item 9]

The surgical operation assisting system according to any one of Items 1 to 8, wherein the score output unit displays the score on a surgical operation monitor.

[Item 10]

The surgical operation assisting system according to Item 3, wherein the score output unit displays whether or not appropriateness is established for the treatment in correspondence with the score.

[Item 11]

The surgical operation assisting system according to any one of Items 1 to 10, wherein the score output unit outputs the score in a case where a variation amount of the score becomes equal to or greater than a predetermined value.

[Item 12]

The surgical operation assisting system according to any one of Items 1 to 11, further including: a treatment possible region display unit that displays a marker indicating a treatment possible region of a surgical operation target on a surgical operation monitor in a superimposed manner.

[Item 13]

The surgical operation assisting system according to Item 12, wherein the treatment possible region display unit displays the score by the marker.

[Item 14]

The surgical operation assisting system according to Item 12 or 13, wherein the marker indicates an approximately outer edge of the treatment possible region.

[Item 15]

The surgical operation assisting system according to any one of Items 1 to 14, wherein a treatment for a surgical operation target includes at least any one among resection, peeling, suture, ligation, and stapling.

[Item 16]

The surgical operation assisting system according to Item 3, 6, 7, 8, 12, 13, 14, or 15, wherein the surgical operation target is a loose connective tissue.

Embodiment 1

Hereinafter, a surgical operation assisting system 1 according to an embodiment of the invention will be described. For example, the surgical operation assisting system 1 of this embodiment assists surgical operation that is performed by remote operation as in an endoscopic surgery or a robot surgical operation.

FIG. 1 is a view illustrating a surgical operation using the surgical operation assisting system 1 of this embodiment. As illustrated in FIG. 1, in this embodiment, it is assumed that a resection organ 3 is resected while preserving a preservation organ 2.

As illustrated in FIG. 1, a specific blood vessel passes through the resection organ 3, and the specific blood vessel 6 exists inside a connective tissue 4, and thus it is necessary to make an incision in the connective tissue 4 so as to treat the specific blood vessel 6. However, in order not to damage the preservation organ 2, the resection organ 3, the specific blood vessel 6, and other living tissues, it is preferable to make an incision in the connective tissue 4 in a state of being stretched. However, on the other hand, when being excessively stretched, rupture may occur in the preservation organ 2 and the other living tissues to which the connective tissue 4 is connected. Therefore, the surgical operation assisting system 1 of this embodiment is trained in advance by accepting a determination of a doctor on that the stretched state of the connective tissue 4 is how much appropriate for conduction of a treatment such as incision, and calculate a score indicating the degree of appropriateness (the degree at which work such as resection can be safely performed with respect to the connective tissue 4) of the state of the connective tissue 4 for the treatment from an image. In addition, during a surgical operation, the score is calculated from an operation field image, and is displayed on a monitor to assist a doctor 110 (hereinafter, also referred to as an operator 110) who treats the connective tissue 4. Note that, in this embodiment, as the treatment, resection is mainly assumed, but the treatment may be peeling, suture, ligation such as clamping, stapling, and the like in addition to the resection.

Examples of the resection organ 3 include a stomach, a large intestine, an esophagus, a pancreas, lungs, a prostate, ovary, and the like. In a case where the resection organ 3 is the stomach, examples of the preservation organ 2 include pancreas, transverse mesocolon, and the like. In a case where the resection organ 3 is the large intestine, examples of the preservation organ 2 include a ureter, an arteriovenous, a seminal vesicle, a pelvic nerve plexus, and the like. In a case where the resection organ 3 is the esophagus, examples of the preservation organ 2 include a trachea, a recurrent laryngeal nerve, and the like. In a case where the resection organ 3 is the pancreas, examples of the preservation organ 2 include a vena realis sinistra, and the like. In a case where the resection organ 3 is the lungs, examples of the preservation organ 2 include the recurrent laryngeal nerve, an aorta, an esophagus, and the like. In a case where the resection organ 3 is the prostate, examples of the preservation organ 2 include a rectum.

The connective tissue 4 (loose connective tissue) exists between the preservation organ 2 and the resection organ 3. A blood is flowing from a main blood vessel 5 to the resection organ 3 through the specific blood vessel 6, and thus in resection of the resection organ 3, when the specific blood vessel 6 needs to be treated, first, the specific blood vessel 6 is exposed by resecting the connective tissue 4 in order to make the treatment of the specific blood vessel 6 easy. Here, in a case where the preservation organ 2 is the stomach, examples of the main blood vessel 5 include a hepatic artery, a celiac artery, and the like, and examples of the specific blood vessel 6 include a gastric artery, and the like. In a case where the preservation organ 2 is the large intestine, examples of the main blood vessel 5 include a portal vein, an aorta, and the like, and examples of the specific blood vessel 6 include an ileocolic artery, an inferior mesenteric artery, and the like. In a case where the preservation organ 2 is the esophagus, examples of the main blood vessel 5 include the aorta and the like. In a case where the preservation organ 2 is the pancreas, examples of the main blood vessel 5 include the portal vein, a superior mesenteric artery, and the like, and examples of the specific blood vessel 6 include IPDA and the like. In a case where the preservation organ 2 is the lungs, examples of the main blood vessel 5 include a trachea, a pulmonary artery, a pulmonary vein, and the like, and the specific blood vessel 6 is, for example, a specific branch of the main blood vessel 5.

In the surgical operation assisting system 1 of this embodiment, information indicating an anatomical state is acquired, and the degree (score) of appropriateness of the anatomical state for treatment is determined, and the score is output. Examples of the anatomical state include a relationship between a plurality of organs (for example, a distance between the preservation organ 2 and the resection organ 3, and the like), a state of organs (for example, a state of the preservation organ 2 and/or the resection organ 3), a state of the loose connective tissue 4 connecting a plurality of tissues (a stretching state, a tensile state, and the like), and the like. In this embodiment, as an example, when resecting the resection organ 3, the resection organ 3 is pulled to be spaced apart from the preservation organ 2, and is tensed to an extent in which rupture does not occur. Whether or not the resection organ 3 is suitable for resection is determined in accordance with this situation. With regard to the score of the anatomical state, an experienced doctor determines the score of the anatomical state from a surgical operation moving image in advance, and a result determined by the doctor can be used in learning by a machine learning method.

<System Configuration>

Figure 2:
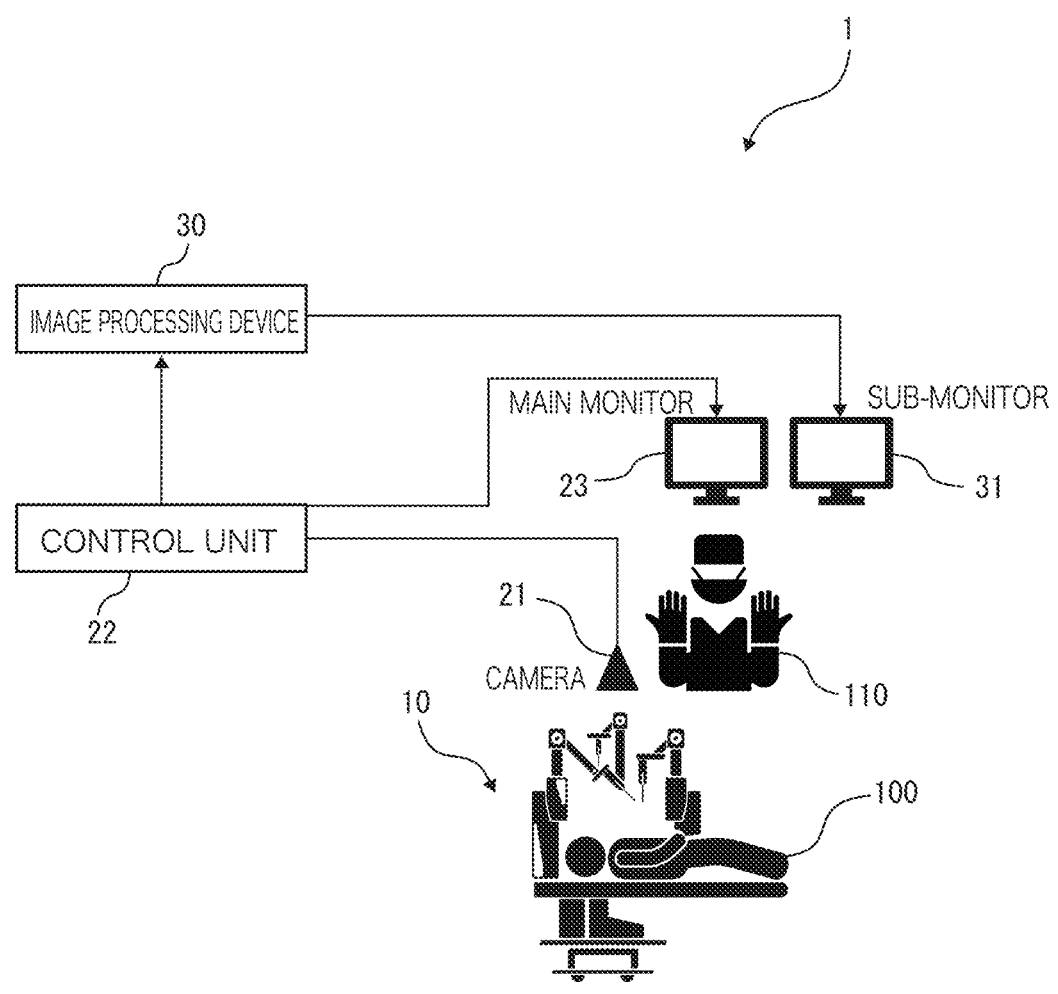
FIG. 2 is a conceptual diagram schematically describing the surgical operation assisting system according to this embodiment.

FIG. 2 is a conceptual diagram schematically illustrating the surgical operation assisting system 1 according to this embodiment. Note that, the configuration in the drawing is illustrative only, and elements other than the configuration may be included.

In the surgical operation assisting system 1, a surgical operation target (patient 100) is placed on a surgical operation unit 10, an operation field of the patient 100 is photographed with a camera 21 (for example, the camera 21 is inserted into an abdomen). The image captured by the camera 21 is received by a control unit 22, and an image output from the control unit 22 is displayed on a main monitor 23. In the surgical operation assisting system 1 of this embodiment, an image processing device 30 acquires the operation field image from the control unit 22, and analyzes the image and outputs a score of the anatomical state to a sub-monitor 31.

<Hardware>

Figure 3:
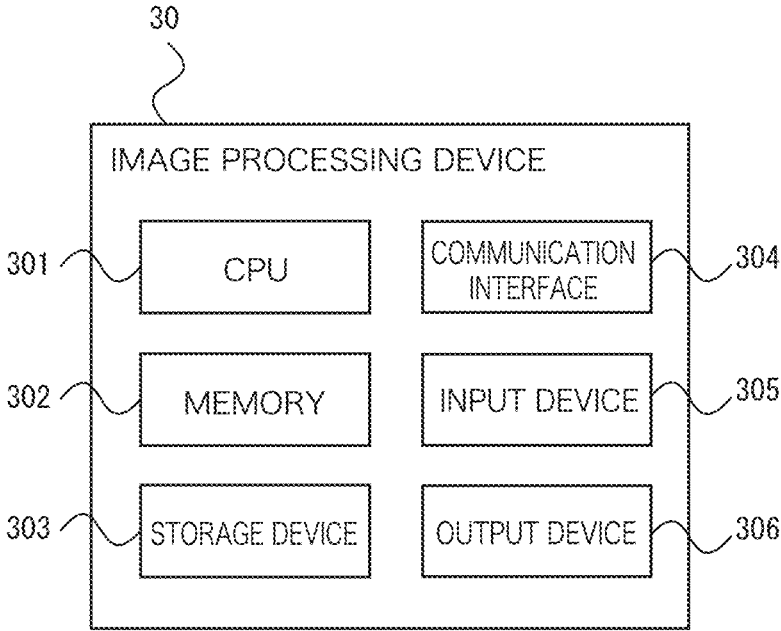
FIG. 3 is a view illustrating a hardware configuration example of an image processing device.

For example, the image processing device 30 may be a general-purpose computer such as a workstation or a personal computer, or may be logically realized by cloud computing. In addition, the image processing device 30 may be a logic circuit such as a field programmable gate array (FPGA). FIG. 3 is a view illustrating a hardware configuration example of the image processing device 30. The image processing device 30 includes a CPU 301, a memory 302, a storage device 303, a communication interface 304, an input device 305, and an output device 306. Examples of the storage device 303 include a hard disk drive, a solid state drive, a flash memory, and the like which store various pieces of data or a program. The communication interface 304 is an interface for connection to a communication network, and examples thereof include an adapter for connection to Ethernet (registered trademark), a modem for connection to a public telephone network, a radio communication device for performing radio communication, a universal serial bus (USB) connector an RS232C connector for serial communication, and the like. Examples of the input device 305 include a keyboard, a mouse, a touch panel, a non-contact panel, a button, a microphone, and the like which input data. Examples of the output device 306 include a display, a printer, a speaker, and the like which output data.

<Software>

Figure 4:
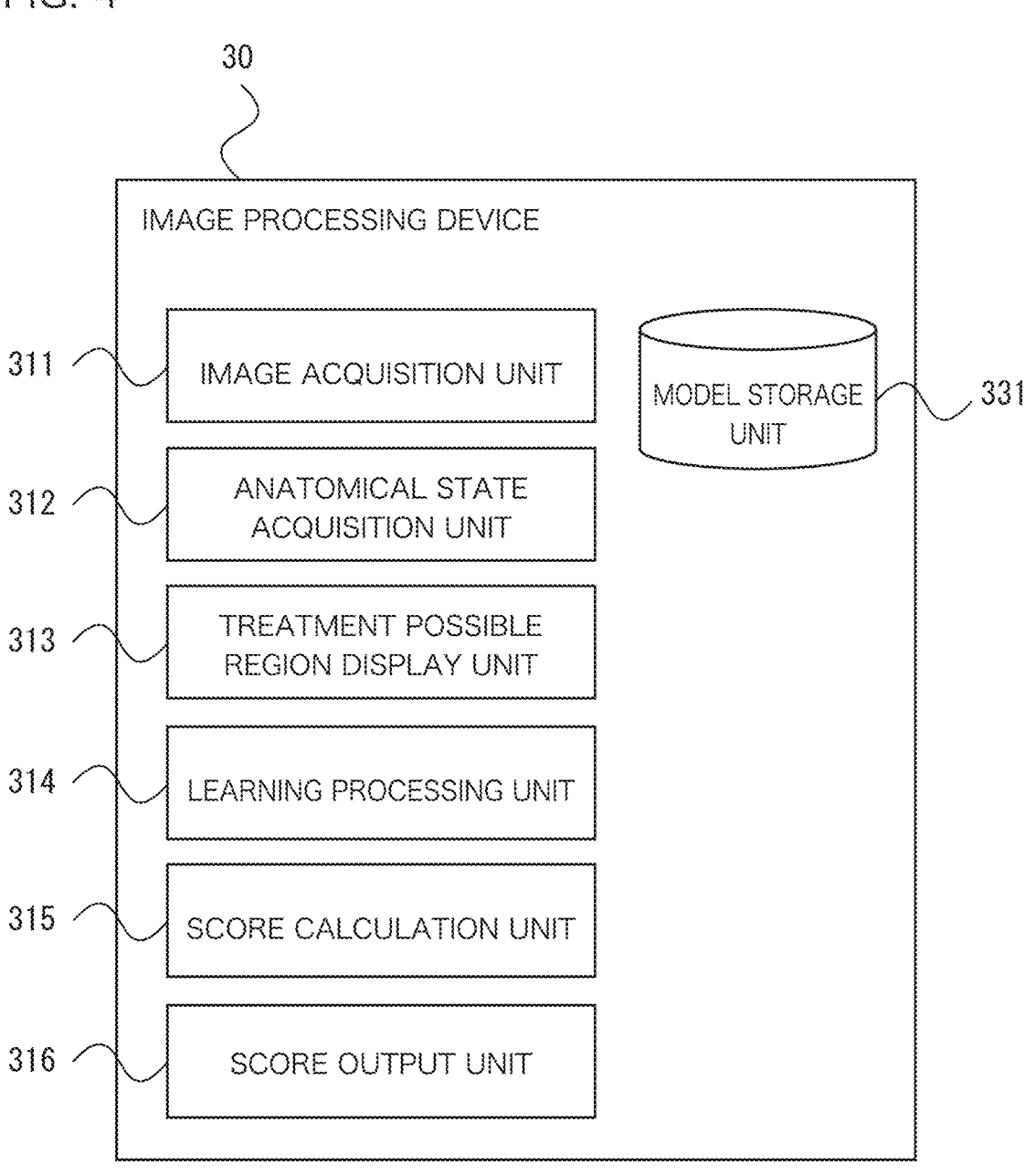
FIG. 4 is a view illustrating a software configuration example of the image processing device.

FIG. 4 is a view illustrating a software configuration example of the image processing device 30. The image processing device 30 includes an image acquisition unit 311, an anatomical state acquisition unit 312, a treatment possible region display unit 313, a learning processing unit 314, a score calculation unit 315, a score output unit 316, and a model storage unit 331.

Note that, in the image processing device 30, the image acquisition unit 311, the anatomical state acquisition unit 312, the treatment possible region display unit 313, the learning processing unit 314, the score calculation unit 315, and the score output unit 316 can be realized when the CPU 301 provided in the image processing device 30 reads out a program stored in the storage device 303 to the memory 302 and executes the program, and the model storage unit 331 can be realized as a part of the memory 302 provided in the image processing device 30 and a storage region provided in the storage device 303.

The image acquisition unit 311 acquires an operation field image captured by the camera 21. In this embodiment, it is assumed that the image acquisition unit 311 acquires a moving image captured by the camera 21 which is output from the control unit 22.

The anatomical state acquisition unit 312 acquires an anatomical state in the operation field. In this embodiment, the anatomical state acquisition unit 312 recognizes living tissues such as an organ, a connective tissue, and a blood vessel by analyzing the image acquired by the image acquisition unit 311, and can acquire, for example, a feature of each living tissue.

The treatment possible region display unit 313 outputs a figure indicating a treatment target tissue (in this embodiment, the connective tissue is assumed) set in advance. For example, the treatment possible region display unit 313 can display the treatment target tissue (for example, the connective tissue) set in advance among living tissues recognized by the anatomical state acquisition unit 312 on an image in a superimposed manner by changing the color of the treatment target tissue or by extracting the contour thereof. In addition, the treatment possible region display unit 313 can be set to output the treatment target tissue only in a case where a score calculated by the score calculation unit 315 to be described later is equal to or greater than a threshold value.

The learning processing unit 314 learns the score corresponding to the anatomical state. For example, the learning processing unit 314 receives an input of a score (can be set in an arbitrary width, for example, a maximum of 5 points, a maximum of 10 points, and a maximum of 100 points) relating to the degree of appropriateness of a state of the treatment target tissue for treatment from a doctor who views an image acquired by the image acquisition unit 311, and can perform learning in a state in which the input score is set as a teaching signal, and the anatomical state (a feature of a living tissue) analyzed from the image is set as an input signal by using, for example, a machine learning method such as a neural network. Note that, the feature applied as the input signal is not limited to the feature of the treatment target tissue. For example, a feature of the preservation organ 2, the resection organ 3, the main blood vessel 5, the specific blood vessel 6, or the like may be employed. That is, for example, the score can be trained in a state of including a positional relationship between the preservation organ 2 and the resection organ 3, or the like. The learning processing unit 314 registers the trained model in the model storage unit 331. The model storage unit 331 stores a model in a known format, and detailed description thereof will be omitted here.

The score calculation unit 315 calculates a score indicating the degree of appropriateness of the treatment target region for treatment on the basis of an image acquired by the image acquisition unit 311. The score calculation unit 315 can calculate the score by applying information (feature) of each living tissue which is acquired by the anatomical state acquisition unit 312 to the model stored in the model storage unit 331.

The score output unit 316 outputs the score calculated by the score calculation unit 315. In this embodiment, the score output unit 316 displays the score on the sub-monitor 31 in a manner of being superimposed on the operation field image captured by the camera 21. The score output unit 316 may output the score to the sub-monitor 31 as character information such as a number, may output a gauge indicating the score in the sub-monitor 31 in the vicinity of a treatment target, or may change the color of a figure displayed by the treatment possible region display unit 313 in correspondence with the score. In addition, the score output unit 316 may output a sound (for example, the sound may be a sound obtained by reading the score by voice synthesis or may be a sound corresponding to the score) representing the score from a speaker.

<Learning Process>

Figure 5:
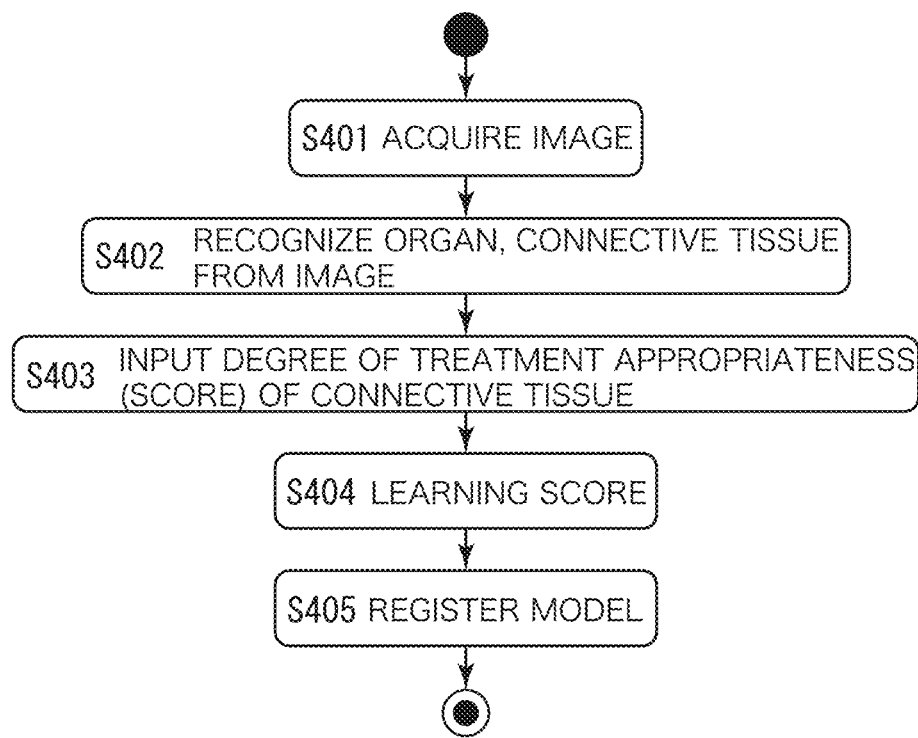
FIG. 5 is a view describing a flow of a learning process in the surgical operation assisting system of this embodiment.

FIG. 5 is a view illustrating a flow of a learning process in the surgical operation assisting system 1 of this embodiment. For example, the learning process illustrated in FIG. 5 may be performed by using the operation field image captured in advance, or may be performed by using an image during photographing.

The image acquisition unit 311 acquires an operation field image (may be an image that is captured in real time, or may be a recorded image) captured by the camera 21 (S401). The anatomical state acquisition unit 312 recognizes living tissues such as the preservation organ 2, the resection organ 3, and the connective tissue 4 from the image (S402), the learning processing unit 314 accepts an input of the score representing the degree of appropriateness of the treatment target tissue (in this embodiment, the connective tissue 4) for treatment from a doctor or the like (S403), learning is performed in a state in which information (a feature or the like) indicating the anatomical state acquired by the anatomical state acquisition unit 312 is set as an input signal, and the received score is set as a teaching signal (S404), and the trained model is registered in the model storage unit 331 (S405).

As described above, the degree of appropriateness (score) of the connective tissue 4 for treatment can be learned from states of respective living tissues such as the preservation organ 2, the resection organ 3, and the connective tissue 4 which are shown in an image on the basis of a captured image of the operation field.

<Learning Process>

Figure 6:
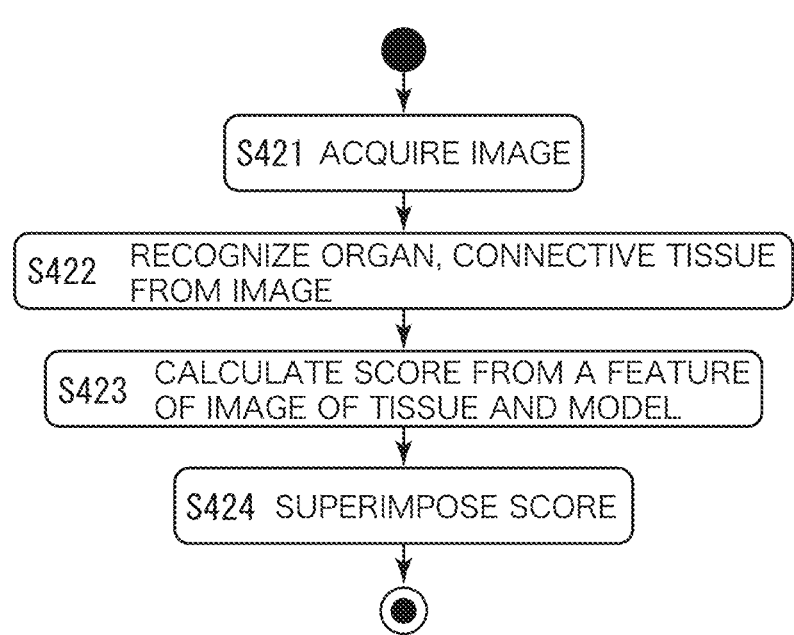
FIG. 6 is a view describing a flow of a score output process in the surgical operation assisting system of this embodiment.

FIG. 6 is a view illustrating a flow of a score output process in the surgical operation assisting system 1 of this embodiment. It is assumed that the score output process illustrated in FIG. 6 is performed on the basis of an image captured during a surgical operation.

The image acquisition unit 311 acquires an operation field image captured by the camera 21 from the control unit 22 (S421). The anatomical state acquisition unit 312 recognizes living tissues such as the preservation organ 2, the resection organ 3, and the connective tissue 4 from the image (S422), and the score calculation unit 315 calculates the score by applying a feature of a recognized tissue to the model stored in the model storage unit 331 (S423). The score output unit 316 displays the calculated score on the sub-monitor 31 in a manner of being superimposed on the operation field image (S424).

As described above, the degree of appropriateness of the treatment target (the connective tissue 4) for treatment can be output to the sub-monitor 31 on the basis of the operation field image captured during the surgical operation.

Figure 7:
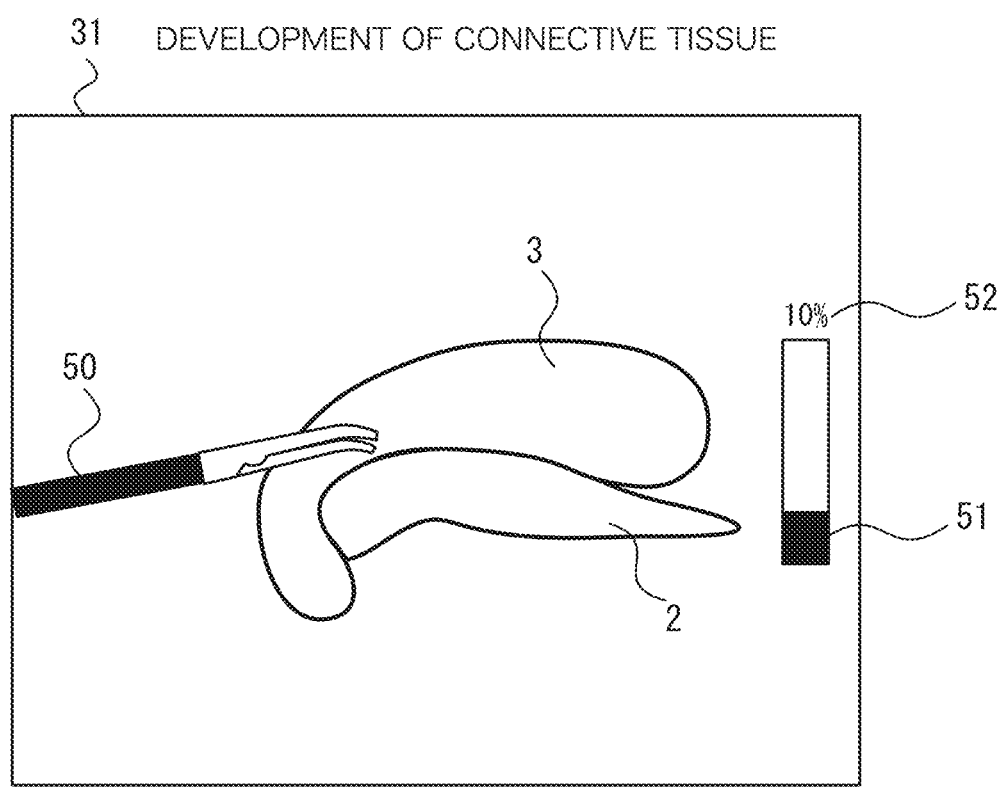
FIG. 7 is a view illustrating a display example of the score relating to a development treatment of a loose connective tissue.
Figure 8:
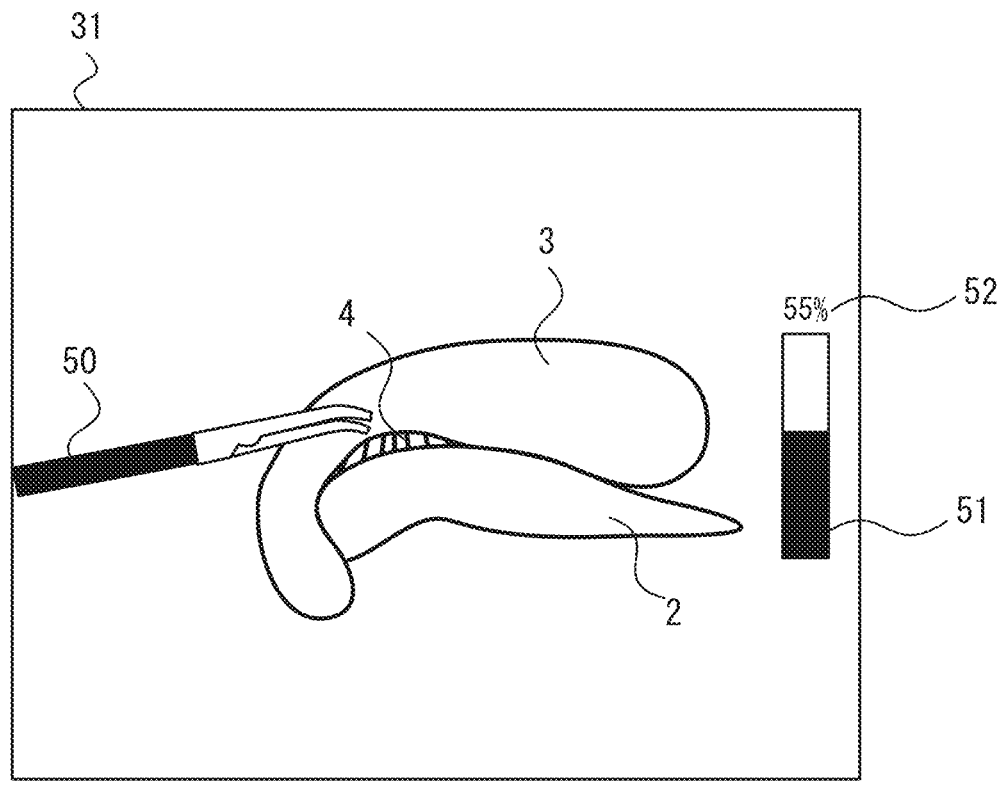
FIG. 8 is a view illustrating the display example of the score relating to the development treatment of the loose connective tissue.
Figure 9:
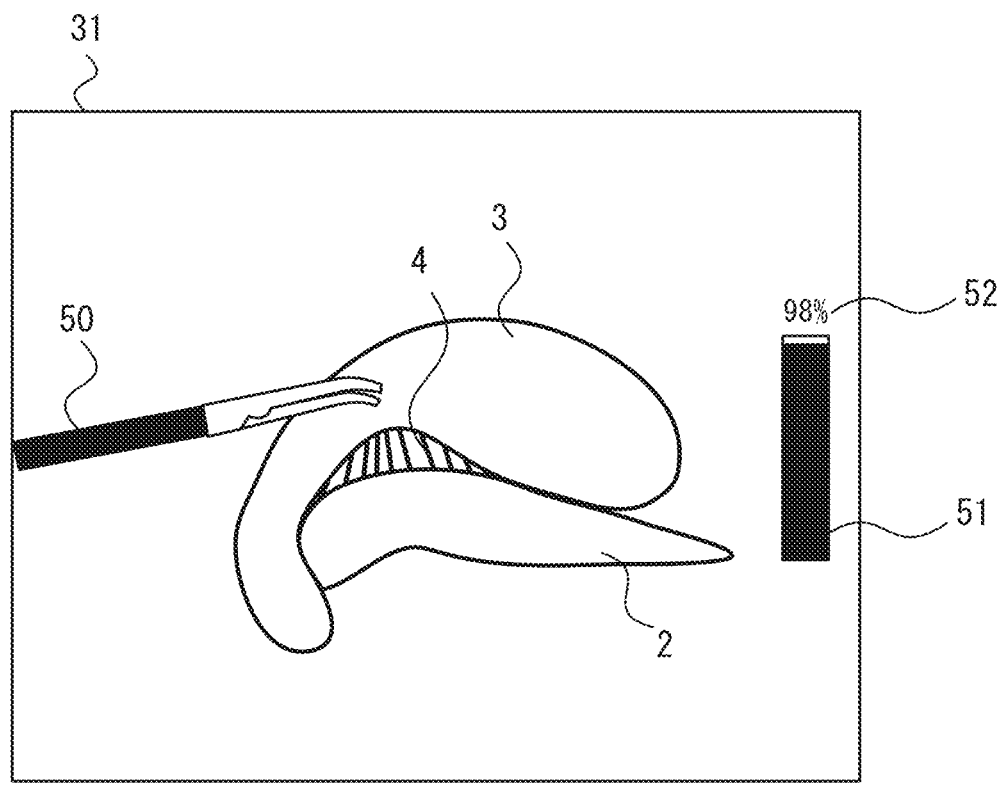
FIG. 9 is a view illustrating the display example of the score relating to the development treatment of the loose connective tissue.

FIG. 7 to FIG. 9 are views illustrating a display example of the score relating to a development treatment of a loose connective tissue. FIG. 7 to FIG. 9 illustrates an example of a case where the connective tissue 4 is the loose connective tissue. The preservation organ 2, the resection organ 3, and the connective tissue 4 therebetween (a case of not being hidden by the preservation organ 2 and the resection organ 3) are displayed on the sub-monitor 31. In addition, in the sub-monitor 31, a score representing the degree of appropriateness of the connective tissue 4 for treatment is displayed in the vicinity of the connective tissue 4 that is a treatment target in a format of a gauge 51 and a character display 52.

In the example in FIG. 7 to FIG. 9, an aspect in which an operator 110 remotely operates a surgical operation instrument 50 to grip the resection organ 3 and to lift up the resection organ 3 to an upper portion of a screen is displayed. The resection organ 3 can be lifted up in the order of FIG. 7, FIG. 8, and FIG. 9, and among the drawings, it can be seen that a state in FIG. 9 is the most appropriate for treatment. As in FIG. 7, in a state in which the resection organ 3 is not separated from the preservation organ 2, the score (the degree of appropriateness for treatment) is shown as 10%, and in FIG. 8, the resection organ 3 can be lifted up, and thus the score is shown as 55%. In the state in FIG. 9, the resection organ 3 can be further lifted up, and thus the score representing the degree of appropriateness for treatment is shown as 98%. The operator 110 (doctor) of the surgical operation can perform treatment such as lifting-up work of the resection organ 3 and resection work of the connective tissue 4 while referencing to the score. In a state in which the resection organ 3 and the preservation organ 2 are separated from each other, and the loose connective tissue is exposed, and is sufficiently stretched and tense, it is known that the loose connective tissue can be safely resected, and safety of the resection can be visually recognized by the gauge 51 and the character display 52, and thus the connective tissue 4 can be safely treated.

In addition, as illustrated in FIG. 8 and FIG. 9, the treatment possible region display unit 313 can display a figure indicating the connective tissue 4 in a manner of being superimposed on an image displayed on the sub-monitor 31. Accordingly, the operator 110 of the surgical operation can instantly and easily recognize the treatment target.

Note that, the score may be displayed by either the gauge 51 or the character display 52, or may express the score by a color of the figure indicating the connective tissue 4 that is being displayed by the treatment possible region display unit 313. For example, in a case where the score is equal to or greater than a first threshold value, the color is set as blue or green, in a case where the score is equal to or less than a second threshold value (smaller than the first threshold value), the color is set as red, and in a case where the score is less than the first threshold value and greater than the second threshold value, the color may be set as yellow. In addition, the color may be a gradation of a color corresponding to the score.

In FIG. 7 to FIG. 9, an example in which the connective tissue 4 is the loose connective tissue is illustrated, but the connective tissue 4 is not limited to the loose connective tissue, and may be a tissue that binds two or more organs. For example, a tight connective tissue is also the connective tissue 4, and a blood vessel can also be grasped as the connective tissue 4. In addition, in the above-described embodiment, it is assumed that the connective tissue 4 is resected, but there is no limitation to resection as long as the treatment is treatment for the connective tissue 4. For example, with regard to the blood vessel 4, treatment such as clipping, resection, and suture can be assumed.

Figure 10:
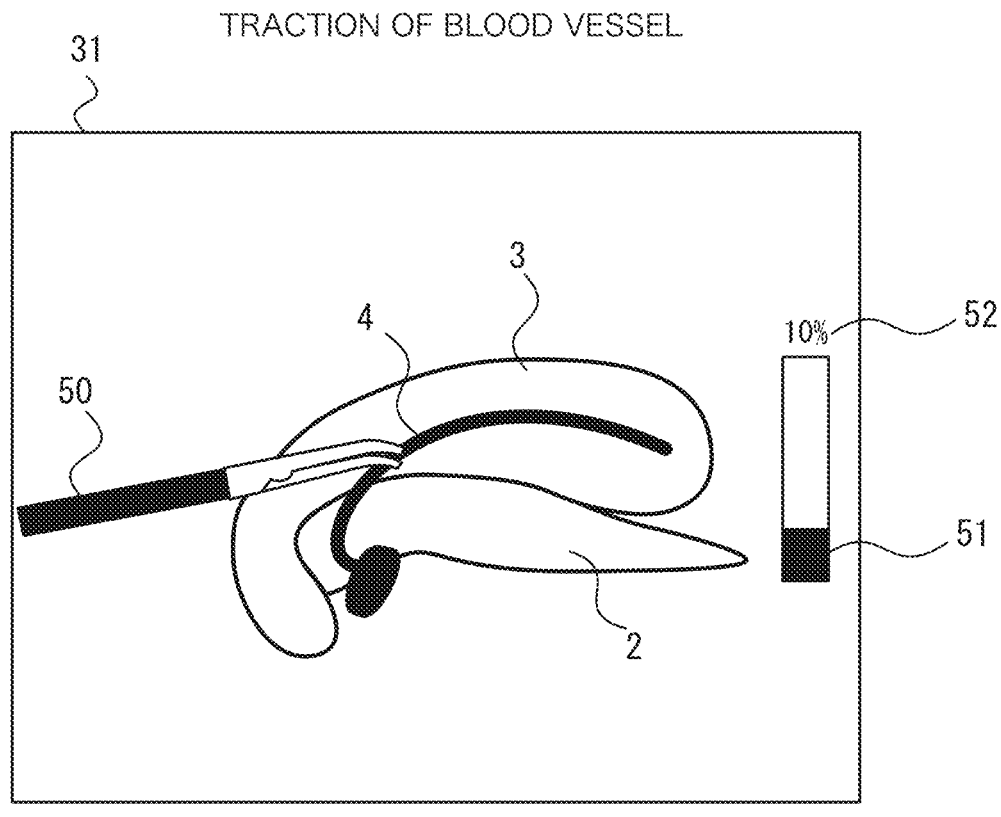
FIG. 10 is a view illustrating a display example of a score relating to traction of a blood vessel.
Figure 11:
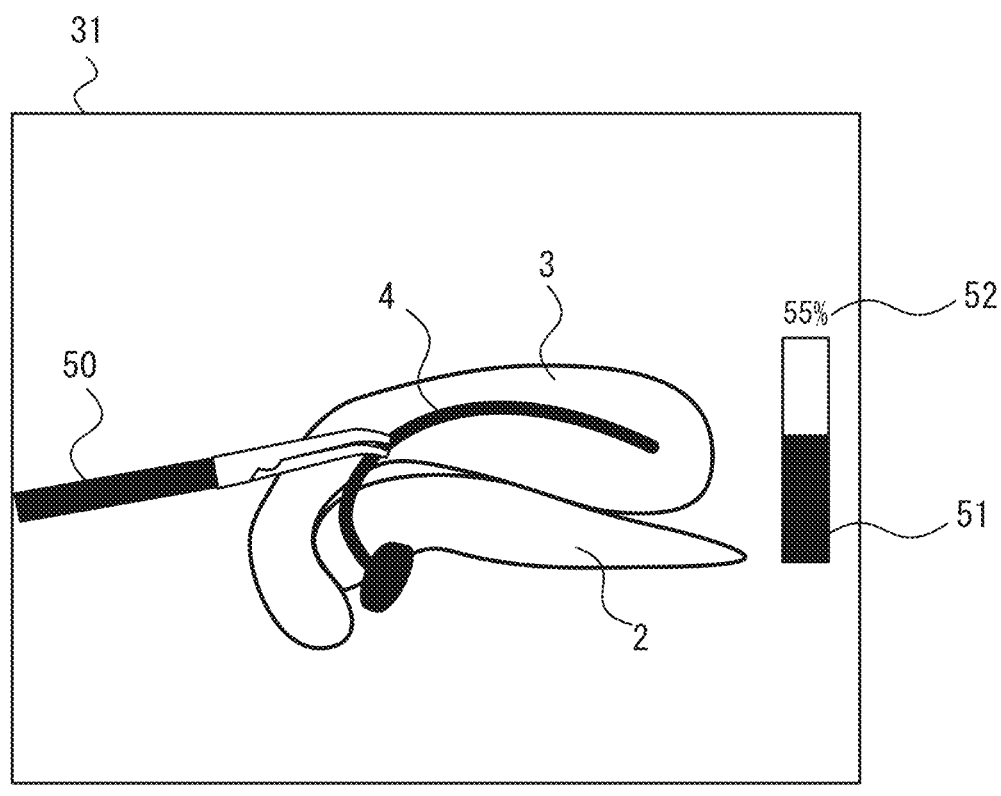
FIG. 11 is a view illustrating the display example of the score relating to traction of the blood vessel.
Figure 12:
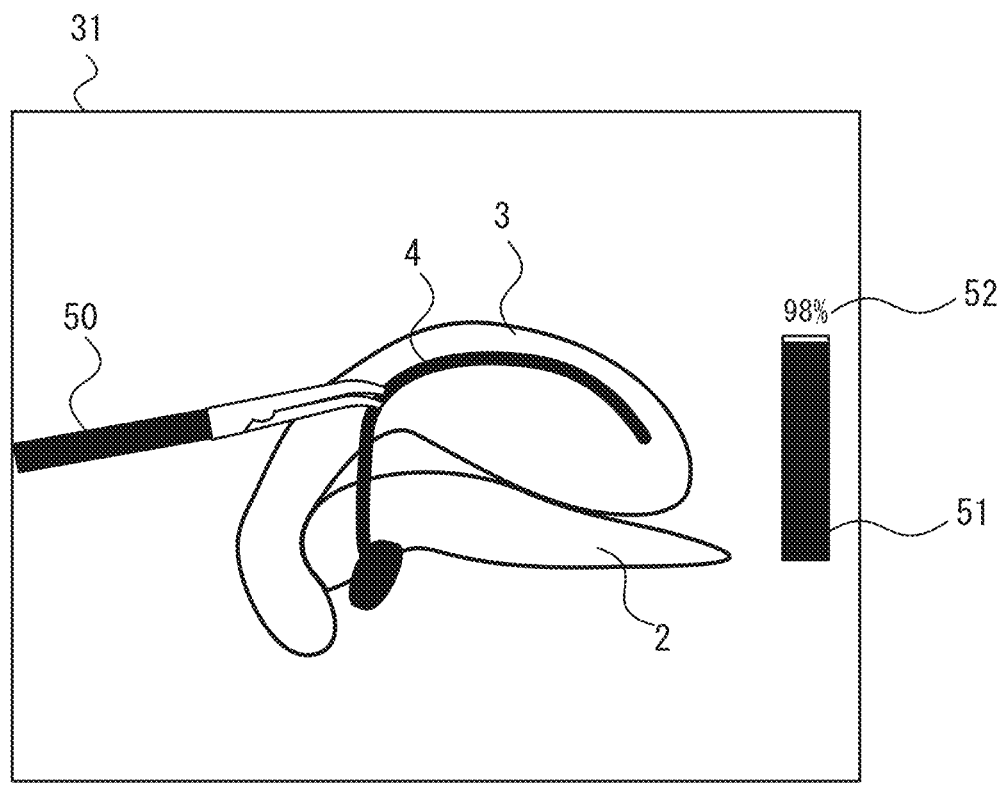
FIG. 12 is a view illustrating the display example of the score relating to traction of the blood vessel.

FIG. 10 to FIG. 12 are views illustrating a display example of a score relating to traction of a blood vessel. In the sub-monitor 31, the preservation organ 2, the resection organ 3, and the blood vessel 4 that passes through therebetween are displayed, and a score indicating the degree of appropriateness of the blood vessel 4 for treatment is displayed in the vicinity of the blood vessel (or the preservation organ 2 or the resection organ 3) in a format of the gauge 51 and the character display 52. In addition, in the example in FIG. 10 to FIG. 12, the connective tissue 4 (blood vessel) instead of the resection organ 3 is stretched by the surgical operation instrument 50. It can be seen that the blood vessel 4 is stretched in the order of FIG. 10, FIG. 11, and FIG. 12. Among the drawings, it can be grasped that a state in FIG. 12 is a state that is most appropriate for treatment. As described above, even for the blood vessel 4, safe treatment can be performed by displaying the degree of appropriateness for the treatment.

As described above, according to the surgical operation assisting system 1 of this embodiment, whether or not an organ that is a treatment target or the like is in a state appropriate for treatment, that is, whether or not the organ or the like is in a state capable of performing safe treatment can be displayed by the score on the basis of a captured image of the operation field. Accordingly, the surgical operation for the treatment target can be safely performed.

Hereinafter, description will be given of a configuration in which information on the connective tissue 4 between the preservation organ 2 and the resection organ 3 is acquired by using a learning model, and navigation information when treating the connective tissue 4 between the preservation organ 2 and the resection organ 3 is output on the basis of the acquired information. In the following embodiment, description will be given by mainly taking the loose connective tissue as an example of the connective tissue 4, but the connective tissue 4 may include a membrane, a layer, an adipose tissue, or the like existing between the preservation organ 2 and the resection organ 3.

Embodiment 2

In Embodiment 2, description will be given of a configuration in which the loose connective tissue between the preservation organ 2 and the resection organ 3 is recognized by using the learning model, and cutting timing of the loose connective tissue is output as navigation information on the basis of the recognition result.

Figure 13:
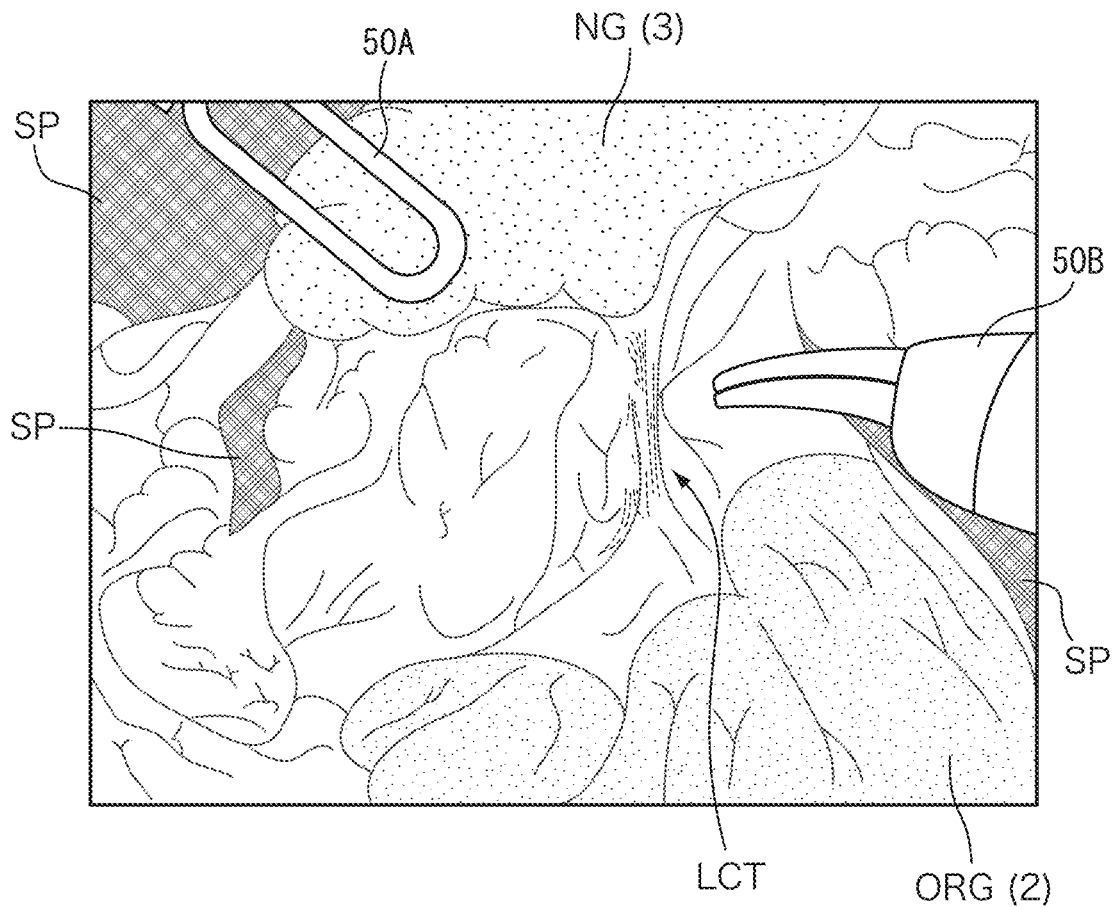
FIG. 13 is a schematic view illustrating an example of an operation field image in Embodiment 2.

FIG. 13 is a schematic view illustrating an example an operation field image in Embodiment 2. A tissue ORG that constitutes the preservation organ 2, a tissue NG that constitutes the resection organ 3, and a loose connective tissue LCT that binds the tissues are included in the operation field illustrated in FIG. 13. The loose connective tissue LCT is an example of the connective tissue 4. In the example in FIG. 13, the loose connective tissue LCT is indicated by a broken line.

In a laparoscopic surgical operation, for example, a surgical operation of removing a lesion site such as malignant tumor formed inside a patient's body is performed. At this time, a doctor grips the tissue NG including the lesion site with forceps 50A, and develops the tissue NG in an appropriate direction to expose the loose connective tissue LCT existing between the tissue NG including the lesion site and the tissue ORG to be left. The doctor resects the exposed loose connective tissue LCT by using an energy treatment tool 50B to peel off the tissue NG including the lesion site from the tissue ORG to be left. The forceps 50A and the energy treatment tool 50B are examples of the surgical operation instrument 50.

Note that, from the viewpoint of easiness of resection of the loose connective tissue LCT, it is preferable that the loose connective tissue LCT that is a resection target has a stretchability. In addition, it is preferable that a space for moving the forceps 50A or the energy treatment tool 50B exists on a depth side of the loose connective tissue LCT that is a resection target. In addition, it is preferable that the loose connective tissue LCT that is a resection target is maintained in a tense state. The example in FIG. 13 illustrates a state in which a space SP exists on a depth side of the loose connective tissue LCT, and at least a part of the loose connective tissue LCT is maintained in a tense state.

Since a humoral substrate or a plurality of kinds of cells exist at the periphery of fibers constituting the loose connective tissue LCT, it is not easy for a doctor to find the loose connective tissue LCT from the operation field image. Therefore, an image processing device 30 according to this embodiment recognizes a loose connective tissue portion from the operation field image by using a learning model 410 (refer to FIG. 14) and outputs assisting information relating to the laparoscopic surgical operation on the basis of the recognition result.

Next, description will be given of a configuration example of the learning model 410 that is used in the image processing device 30.

Figure 14:
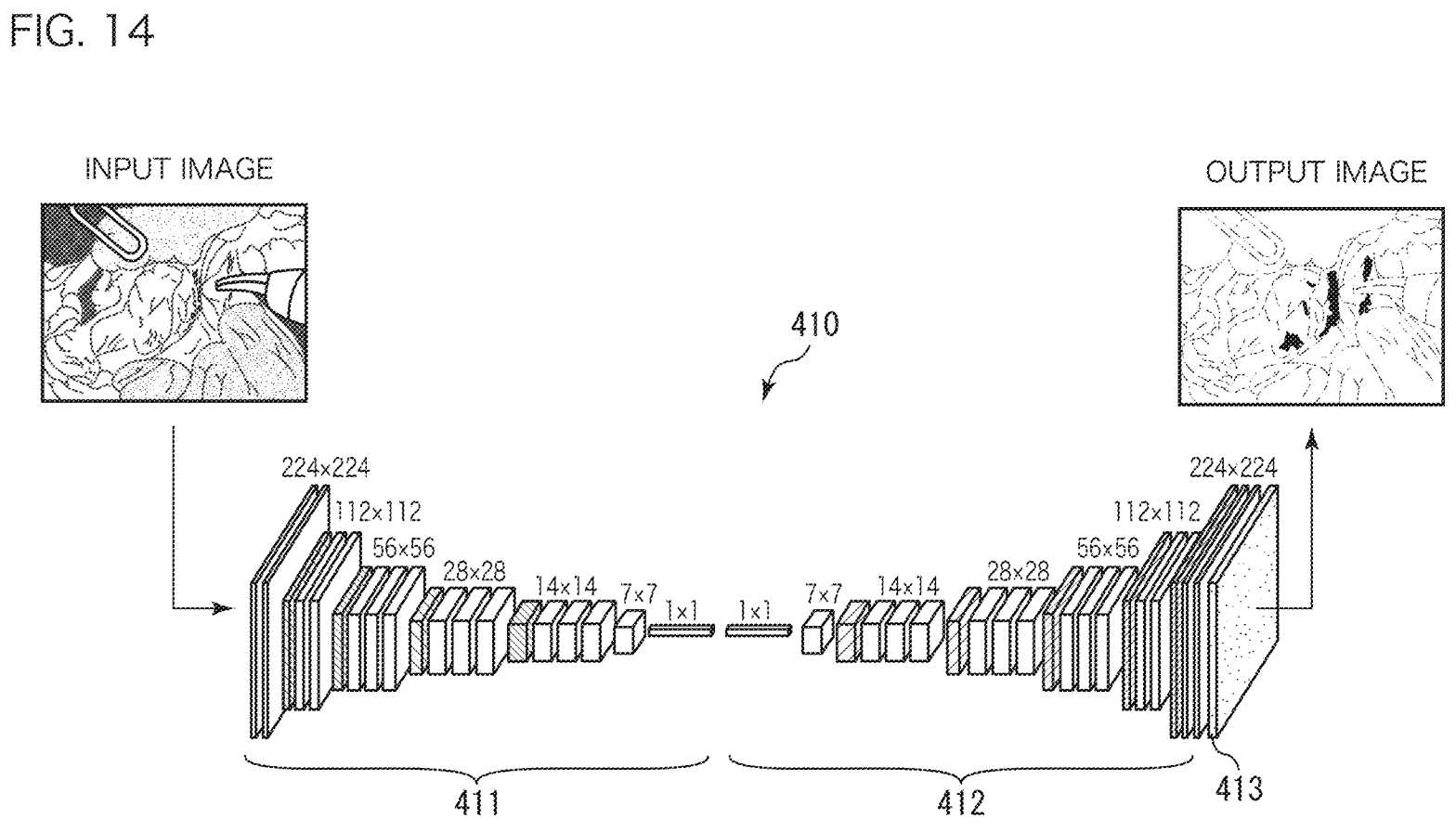

FIG. 14 is a schematic view illustrating a configuration example of the learning model 410. The learning model 410 is a learning model for performing image segmentation, and is constructed by, for example, a neural network including a convolutional layer such as SegNet. FIG. 14 illustrates a configuration example of the SegNet, but the learning model 410 may be constructed by using an arbitrary neural network such as a fully convolutional network (FCN), a U-shaped network (U-Net), and a pyramid scene parsing network (PSPNet) capable of image division without limitation to the SegNet. In addition, the learning model 410 may be constructed by using neural network for object detection such as you only look once (YOLO) and single shot multi-box detector (SSD) instead of the neural network for image division.

In this embodiment, an image input to the learning model 410 is the operation field image obtained from the camera 21. The operation field image may be a still image without limitation to a moving image. In addition, the operation field image that is input to the learning model 410 is not necessary to be a raw image obtained from the camera 21, and may be an image subjected to appropriate image processing, data representing a frequency component of an image, or the like. With respect to an input of the operation field image, the learning model 410 is trained to output an image representing a recognition result of a loose connective tissue portion included in the operation field image.

For example, the learning model 410 in this embodiment includes an encoder 411, a decoder 412, and a soft max layer 413. The encoder 411 is configured by alternately disposing the convolutional layer and a pooling layer. The convolutional layer is formed as a multi layer such as two or three layers. In the example in FIG. 14, the convolutional layer is shown without hatching, and the pooling layer is shown with hatching.

In the convolutional layer, a convolutional operation of input data and a filter having a size (for example, 3×3, 5×5, or the like) determined in each case. That is, an input value that is input to a position corresponding to each element of the filter, and a weight coefficient set to the filter in advance are multiplied for each element, and a linear sum of a multiplication value for each element is calculated. When adding a bias that is set to the calculated linear sum, an output in the convolutional layer is obtained. Note that, a result of the convolutional operation may be converted by an activation function. As the activation function, for example, a rectified linear unit (ReLU) can be used. The output of the convolutional layer represents a feature map obtained by extracting a feature of the input data.

In the pooling layer, a local statistic of the feature map output from the convolutional layer that is an upper layer connected to an input side is calculated. Specifically, a window having a predetermined size (for example, 2×2, 3×3, or the like) corresponding to a position of the upper layer is set, and the local static is calculated from an input value within the window. As the static, for example, a maximum value can be employed. The size of the feature map output from the pooling layer is reduced in correspondence with the size of the window (down-sampling). The example in FIG. 14 illustrates that an input image of 224 pixels×224 pixels is sequentially down-sampled to feature maps of 112×112, 56×56, 28×28, . . . , and 1×1 by sequentially repeating an operation in the convolutional layer and an operation in the pooling layer are sequentially repeated in the encoder 411.

An output (in the example in FIG. 14, a feature map of 1×1) of the encoder 411 is input to the decoder 412. The decoder 412 is constructed by alternately arranging a transposed convolutional layer and a transposed pooling layer. The transposed convolutional layer is formed as a multi-layer such as two layers or three layers. In the example in FIG. 14, the transposed convolutional layer is shown without hatching and the transposed pooling layer is shown with hatching.

In the transposed convolutional layer, a transposed convolutional operation is performed with respect to an input feature map. The transposed convolutional operation is an operation of restoring a feature map before the convolutional operation on the assumption that the input feature map is a result obtained by a convolutional operation by using a specific filter. In the operation, when the specific filter is expressed by a matrix, the product of a transposed matrix for the matrix and the input feature map is calculated to generate a feature map for output. Note that, the operation result of the transposed convolutional layer may be converted by the above-described activation function such as ReLU.

The transposed pooling layer provided in the decoder 412 is individually associated with the pooling layer provided in the encoder 411 in a one-to-one manner, and an associated pair has substantially the same size. The transposed pooling layer enlarges the size of the feature map that is down-sampled in the pooling layer of the encoder 411 again (up sampling). The example of FIG. 14 illustrates sequential up-sampling to a feature map of 1×1, 7×7, 14×14, . . . , and 224×224 by sequentially repeating an operation in the convolutional layer and an operation in the pooling layer in the decoder 412.

An output (in the example in FIG. 14, the feature map of 224×224) of the decoder 412 is input to the soft max layer 413. The soft max layer 413 outputs a probability of a label that identifies a portion at each position (pixel) by applying a soft max function to an input value from the transposed convolutional layer connected to an input side. In this embodiment, a label that identifies a loose connective tissue is set, and whether or not the label belongs to the loose connective tissue may be identified in a pixel unit. When extracting a pixel in which the probability of the label output from the soft max layer 413 is equal to or greater than a threshold value (for example, 50% or greater), an image (hereinafter, referred to as recognition image) indicating a recognition result of the loose connective tissue portion is obtained.

Note that, in the example in FIG. 14, an image of 224 pixels×224 pixels is set as an input image to the learning model 410, but the size of the input image is not limited to the above-described size, and can be appropriately set in correspondence with processing capacity of the image processing device 30, the size of the operation field image obtained from the camera 21, and the like. In addition, it is not necessary for the input image to the learning model 410 to be the entirety of the operation field image obtained from the camera 21, and the input image may be a partial image generated by cutting an attention region of the operation field image. The attention region including a treatment target is frequently located near the center of the operation field image, and thus for example, a partial image obtained by cutting out the vicinity of the center of the operation field image in a rectangular shape so as to be approximately the half of the original size may be used. When reducing the size of the image that is input to the learning model 410, recognition accuracy can be raised while raising a processing speed.

Figure 15:
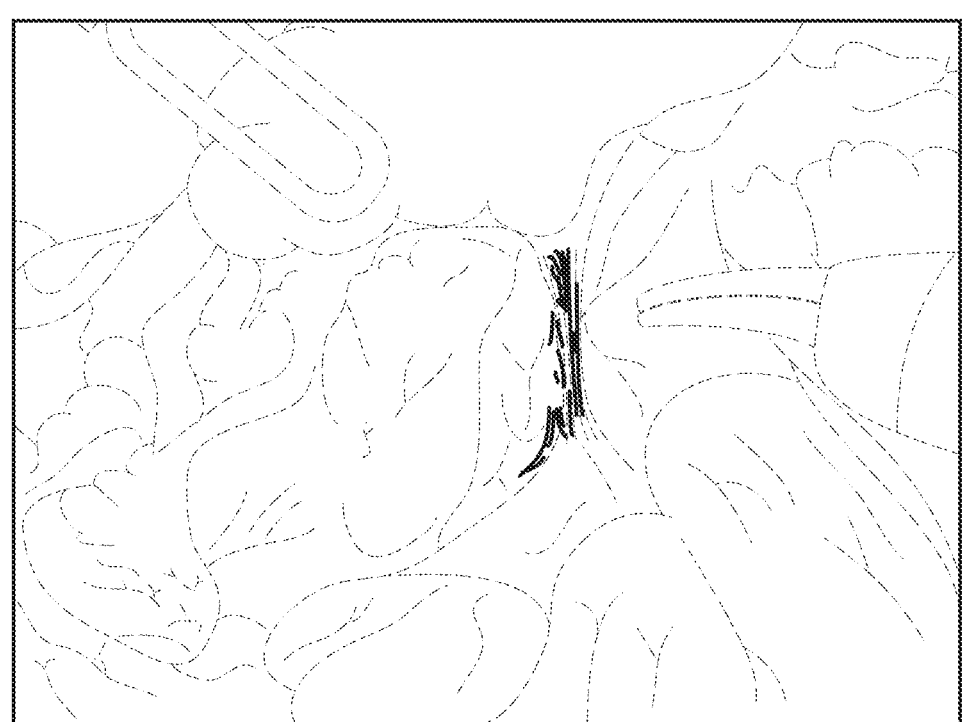
FIG. 15 is a schematic view illustrating a recognition result obtained by the learning model.

FIG. 15 is a schematic view illustrating a recognition result obtained by the learning model 410. In the example in FIG. 15, a loose connective tissue portion recognized by using the learning model 410 is indicated by a bold solid-line, and the other organs or tissue portions are indicated by a broken line for reference. The CPU 301 of the image processing device 30 generates a recognition image of the loose connective tissue to discriminately display the recognized loose connective tissue portion. The recognition image is an image having the same size as in the operation field image, and an image obtained by allocating a specific color to a pixel recognized as the loose connective tissue. It is preferable that the color that is allocated to the pixel of the loose connective tissue is a color that does not exist inside a human body so as to be discriminated from organs, blood vessels, and the like. Examples of the color that does not exist inside the human body include a color of a cold color system (blue color system) such as blue or aqua blue. In addition, information indicating a transmittance is applied to each pixel constituting the recognition image, and a non-transmission value is set to a pixel recognized as the loose connective tissue, and a transmission value is set to the other pixels. When arranging the recognition image generated as described above in a manner of being superimposed on the operation field image, the recognition image can be displayed on the operation field image as a structure in which the loose connective tissue portion has a specific color.

For example, the image processing device 30 generates the learning model 410 in a learning phase before initiation of operation. As a preparatory step for generating the learning model 410, in this embodiment, annotation is performed with respect to the operation field image obtained from the camera 21 by manually dividing the loose connective tissue portion. Note that, in the annotation, an operation field image stored in the storage device 303 or the like may be used.

When performing the annotation, a worker (a professional such as a doctor) finds out a loose connective tissue that exists between a preservation organ and a resection organ and is in an easy resection situation while displaying the operation field image on the sub-monitor 31 in time series. Specifically, a loose connective tissue in an exposed state after developing a tissue including a lesion site is found. It is preferable that exposed loose connective tissue has stretchability, and is maintained in a tense state. In addition, it is preferable that a space exists on a depth side of the loose connective tissue for moving the surgical operation instrument 50. In a case of fining a loose connective tissue that is in an easy resection situation, a worker performs annotation by selecting a portion corresponding to the loose connective tissue in a pixel unit in the operation field image by using a mouse, a stylus pen, or the like provided in the input device 305. In addition, a loose connective tissue running pattern suitable for learning may be selected, and the number of data may be increased by processing such as perspective conversion or reflection. In addition, when the learning progresses, the number of data may be increased by using a recognition result obtained by the learning model 410.

When the annotation is performed with respect to a plurality of operation field images, training data composed of a set of the operation field image and correct answer data representing the loose connective tissue portion in the operation field image is prepared. The training data is stored in a storage device (for example, the storage device 303 of the image processing device 30).

Figure 16:
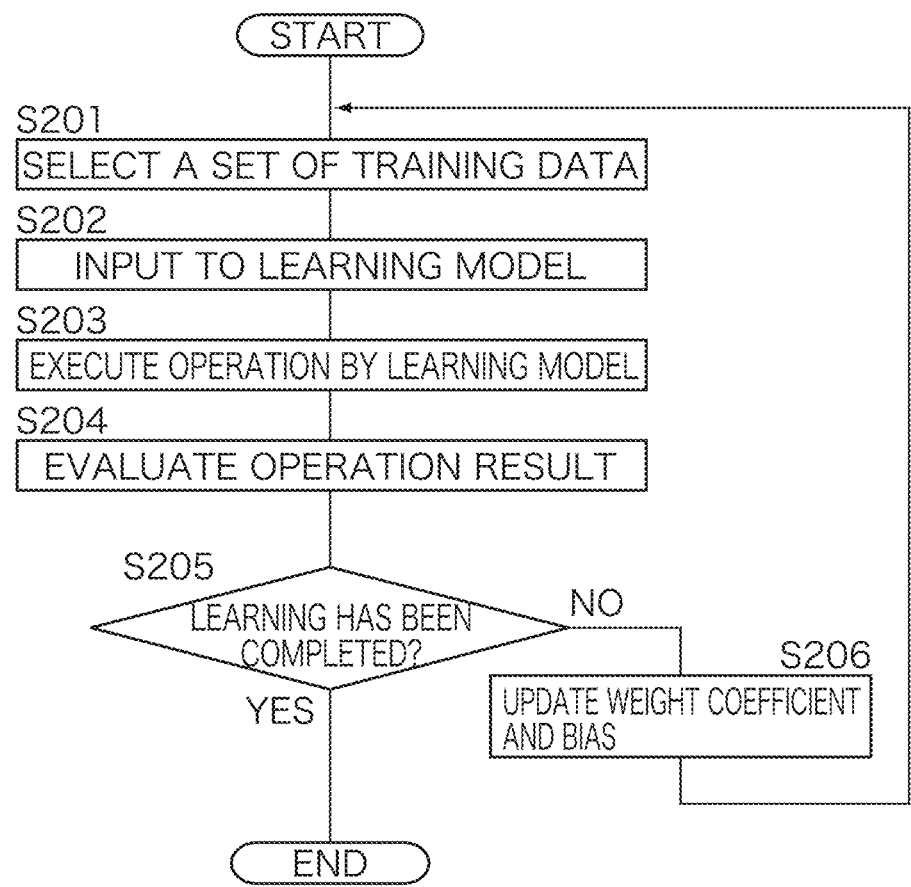
FIG. 16 is a flowchart describing a generation procedure of the learning model.

FIG. 16 is a flowchart illustrating a generation procedure of the learning model 410. The CPU 301 of the image processing device 30 reads out a learning program prepared in advance from the storage device 303, and executes the following procedure to generate the learning model 410. Note that, it is assumed that at a stage before initiating learning, an initial value is given to definition information describing the learning model 410.

The CPU 301 accesses the storage device 303 and selects a set of training data that is used in learning (step S201). The CPU 301 inputs an operation field image included in the selected training data to the learning model 410 (step S202), and executes an operation by the learning model 410 (step S203). That is, the CPU 301 generates a feature map from the input operation field image, and executes an operation of sequentially down-sampling the generated feature map by the encoder 411, an operation of sequentially up-sampling the feature map input from the encoder 411 by the decoder 412, and an operation of identifying each pixel of the feature map that is finally obtained from the decoder 412 by the soft max layer 413.

The CPU 301 acquires an operation result from the learning model 410, and evaluates the acquired operation result (step S204). For example, the CPU 301 may evaluate the operation result by calculating similarity between image data of the loose connective tissue portion that is obtained as a result of the operation, and correct answer data included in the training data. For example, the similarity is calculated by a Jaccard coefficient. When the loose connective tissue portion extracted by the learning model 410 is set as A, and the loose connective tissue portion included in the correct answer data is set as B, the Jaccard coefficient is given by $A \cap B / A \cap B \times 100(\%)$. A Dice coefficient or a Simpson coefficient may be calculated instead of the Jaccard coefficient, and the similarity may be calculated by using the other existing methods.

The CPU 301 determines whether or not learning has been completed on the basis of evaluation for the operation result (step S205). In a case where similarity equal to or greater than a threshold value set in advance is obtained, the CPU 301 can determine that learning has been completed.

In a case where it is determined that learning is not completed (S205: NO), the CPU 301 sequentially updates a weight coefficient and a bias in each layer of the learning model 410 from an output side of the learning model 410 to an input side thereof by using an inverse error propagation method (step S206). After updating the weight coefficient and the bias of each layer, the CPU 301 returns the process to step S201, and executes the processes from step S201 to step S205 again.

In step S205, in a case where it is determined that learning has been completed (S205: YES), the learning model 410 that is trained is obtained, and thus the CPU 301 stores the obtained learning model 410 in the model storage unit 331, and terminates the process by this flow chart.

In this embodiment, the image processing device 30 is configured to generate the learning model 410, but the learning model 410 may be generated by an external computer such as a server device. The image processing device 30 may acquire the learning model 410 generated by the external computer with communication or the like, and may store the acquired learning model 410 in the model storage unit 331.

Figure 17:
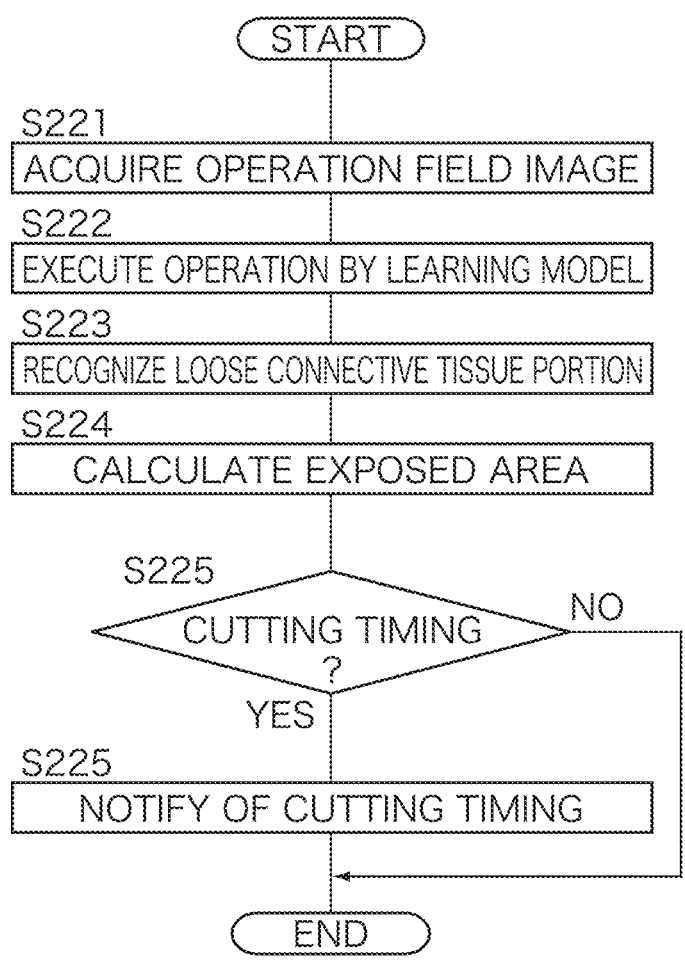
FIG. 17 is a flowchart describing a procedure that is executed in an operation phase by an image processing device according to Embodiment 2.

The image processing device 30 executes the following process in an operation phase after the trained learning model 410 is obtained. FIG. 17 is a flowchart describing a procedure that is executed in an operation phase by the image processing device 30 in Embodiment 2. The CPU 301 of the image processing device 30 reads out a recognition processing program prepared in advance from the storage device 303 and executes the recognition processing program to execute the following procedure. When a laparoscopic surgical operation is initiated, an operation field image obtained by imaging an operation field is output from the camera 21 to the control unit 22 at any time. The CPU 301 of the image processing device 30 acquires the operation field image output from the control unit 22 through the image acquisition unit 311 (step S221). The CPU 301 executes the following process whenever the operation field image is acquired.

The CPU 301 inputs the acquired operation field image to the learning model 410, executes an operation using the learning model 410 (step S222), and recognizes a loose connective tissue portion included in the operation field image (step S223). That is, the CPU 301 generates a feature map from the input operation field image, and executes an operation of sequentially down-sampling the generated feature map by the encoder 411, an operation of sequentially up-sampling the feature map input from the encoder 411 by the decoder 412, and an operation of identifying each pixel of the feature map that is finally obtained from the decoder 412 by the soft max layer 413. In addition, the CPU 301 recognizes a pixel in which the probability of label output from the soft max layer 413 is equal to or greater than a threshold value (for example, 50% or greater) as the loose connective tissue portion.

Then, the CPU 301 calculates an exposed area of the loose connective tissue portion on the basis of the recognition result obtained by the learning model 410 (step S224). The CPU 301 may calculate the number of pixels recognized as the loose connective tissue, or a ratio of the pixels recognized as the loose connective tissue among the entirety of pixels in the operation field image as the exposed area. In addition, the CPU 301 may derive distance information up to a focal point, for example, with reference to a focal length of the camera 21 or the like, and may correct the exposed area on the basis of the derived distance information in order to standardize the size (area) per one pixel.

Then, the CPU 301 determines whether or not it is cutting timing of the loose connective tissue on the basis of the calculated exposed area (step S225). Specifically, the CPU 301 determines a magnitude relationship between the calculated exposed area and a threshold value that is set in advance, and when the exposed area is greater than the threshold value, the CPU 301 may determine that timing is the cutting timing. In a case where it is not determined as the cutting timing (S225: NO), the CPU 301 terminates the process according to this flowchart.

In a case where it is determined that timing is the cutting timing (S225: YES), the CPU 301 gives a notification indicating the cutting timing of the loose connective tissue (step S226). For example, the CPU 301 can display character information indicating the cutting timing of the loose connective tissue in a manner of being superimposed on the operation field image. Instead of the configuration in which the character information is displayed, an icon or a record indicating the cutting timing of the loose connective tissue may be displayed in a manner of being superimposed on the operation field image. In addition, the CPU 301 may output the gist indicating the cutting timing through a microphone provided in the output device 306, or in a case where a vibrator is mounted to a laparoscope or a surgical operation instrument, the CPU 301 may give a notification of the cutting timing by causing the vibrator to vibrate.

In addition, since the loose connective tissue is recognized in step S223, the CPU 301 may generate a recognition image and may display the generated recognition image in a manner of being superimposed on the operation field image. For example, the CPU 301 may allocate a color (for example, a color of a cold color system (blue color system)) such as blue or an aqua color that does not exist inside the human body to a pixel recognized as the loose connective tissue, and may set a transmittance to pixels other than the loose connective tissue so that the background is transmitted to generate the recognition image. In addition, since the exposed area of the loose connective tissue is calculated in step S224, the CPU 301 may generate an indicator image representing the magnitude of the exposed area, and may display the generated indicator image in a manner of being superimposed on the operation field image.

Figure 18:
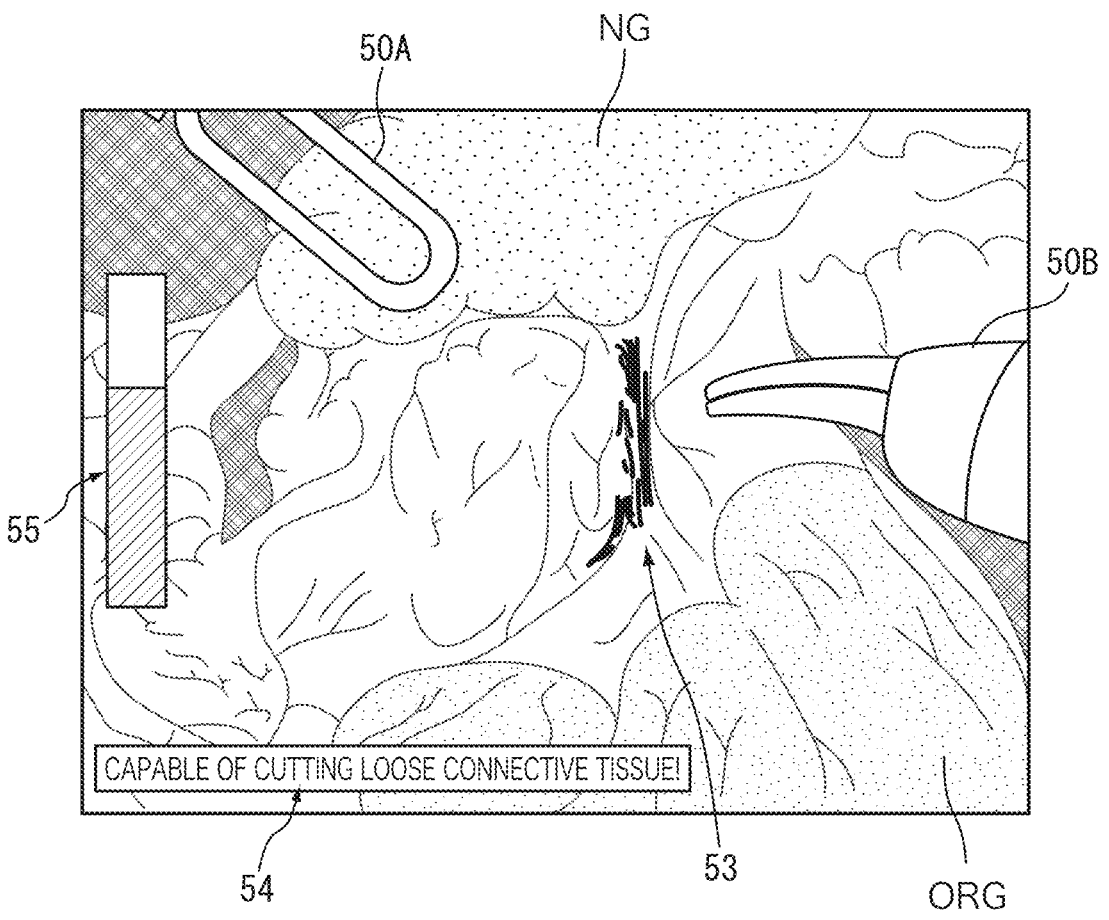
FIG. 18 is a schematic view illustrating a display example according to Embodiment 2.

FIG. 18 is a schematic view illustrating a display example in Embodiment 2. FIG. 18 illustrates an example in which a recognition image 53 of the loose connective tissue, character information 54 indicating cutting timing of the loose connective tissue, and an indicator 55 indicating the magnitude of an exposed area of the loose connective tissue are displayed in a manner of being superimposed on the operation field image illustrated in FIG. 13. It is not necessary for the image processing device 30 to display the information always, and the information may be displayed only in a case where a display instruction is given from a doctor through the input device 305 or a foot switch (not illustrated).

As described above, in Embodiment 2, the loose connective tissue portion included in the operation field image is recognized by using the learning model 410, and information indicating that timing is the cutting timing of the loose connective tissue is output on the basis of the recognition result. With regard to a process of cutting the loose connective tissue between the tissue ORG constituting the preservation organ 2 and the tissue NG constituting the resection organ 3, the image processing device 30 outputs the navigation information to perform visual assistance for a doctor.

In Embodiment 2, whether or not timing is the cutting timing is determined in correspondence with the exposed area of the loose connective tissue. However, the loose connective tissue in a tense state may be recognized by using the learning model 410, and whether or not timing is the cutting timing may be determined in correspondence with the recognition result. For example, annotation may be performed by selecting the loose connective tissue portion in a tense state in a pixel unit, and training data obtained by the annotation may be used to generate the learning model 410 that recognizes the loose connective tissue in a tense state. The CPU 301 of the image processing device 30 may input the operation field image captured by the camera 21 to the learning model 410 and may execute an operation using the learning model 410 to recognize loose connection in a tense state. In a case of recognizing the loose connective tissue in a tense state by using the learning model 410, the CPU 301 may give a notification of character information or the like that indicates cutting timing.

The image processing device 30 in Embodiment 2 includes the learning model 410, but may further include learning models 420 to 450 to be described later. That is, the image processing device 30 may be configured to generate the navigation information by using a combination of a plurality of learning models.

Embodiment 3

In Embodiment 3, description will be given of a configuration in which the loose connective tissue between the preservation organ 2 and the resection organ 3 is recognized by using the learning model 410, and information on an operation at the timing of treating the loose connective tissue is output as the navigation information on the basis of the recognition result.

The image processing device 30 inputs the operation field image to the learning model 410, and executes an operation by the learning model 410 to recognize the loose connective tissue portion included in the operation field image. The image processing device 30 in Embodiment 3 determines an operation direction of the surgical operation instrument 50 when developing or cutting the loose connective tissue with reference to the recognition result by the learning model 410, and outputs information on the determined operation direction.

Figure 19:
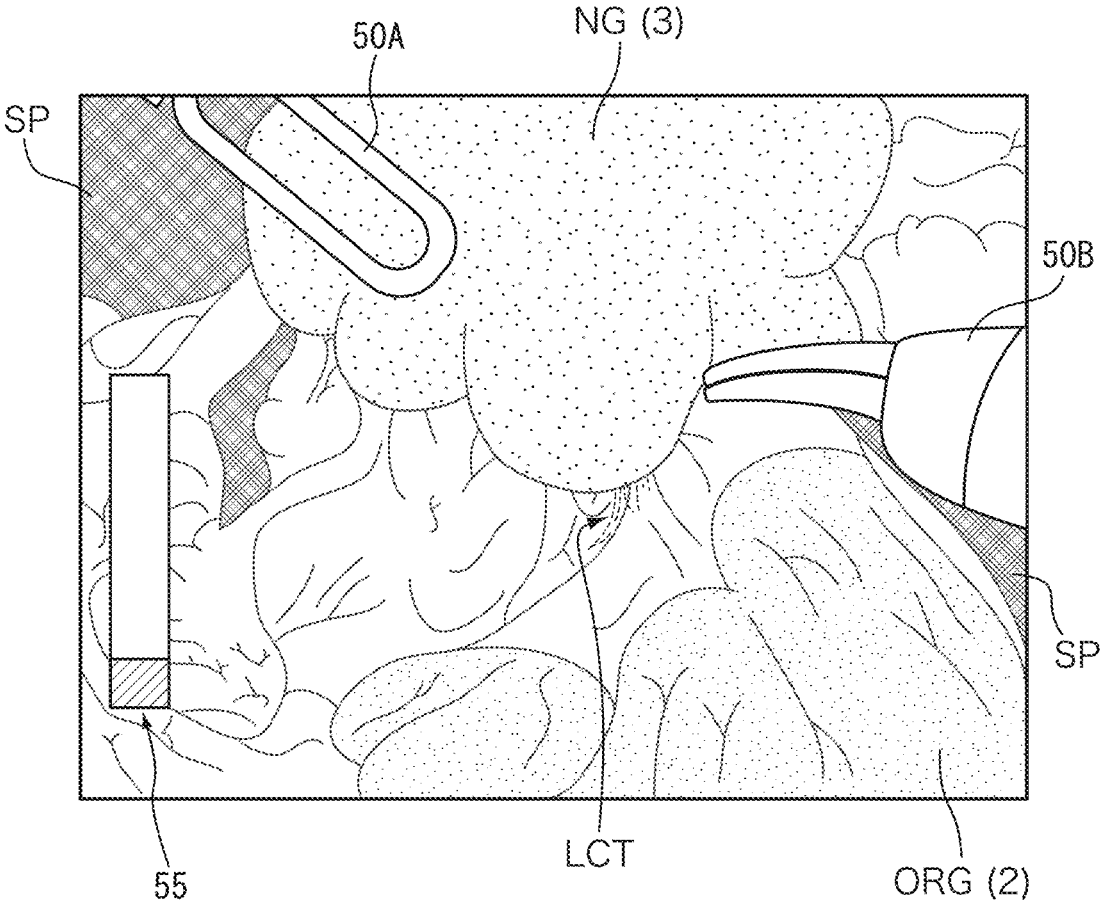
FIG. 19 is a schematic view illustrating an example of an operation field image for which a development operation is required.

FIG. 19 is a schematic view illustrating an example of the operation field image for which the development operation is required. FIG. 19 illustrates an operation field image in a state in which the loose connective tissue is not sufficiently developed. The image processing device 30 inputs the operation field image to the learning model 410, and executes an operation by the learning model 410 to recognize existence of the loose connective tissue LCT that starts to be exposed from an edge end portion of the resection organ 3. However, as indicated by the indicator 55, since the loose connective tissue LCT does not have a sufficient exposed area, it can be seen that the loose connective tissue LCT is necessary to be further developed so as to be cut out.

Figure 20:
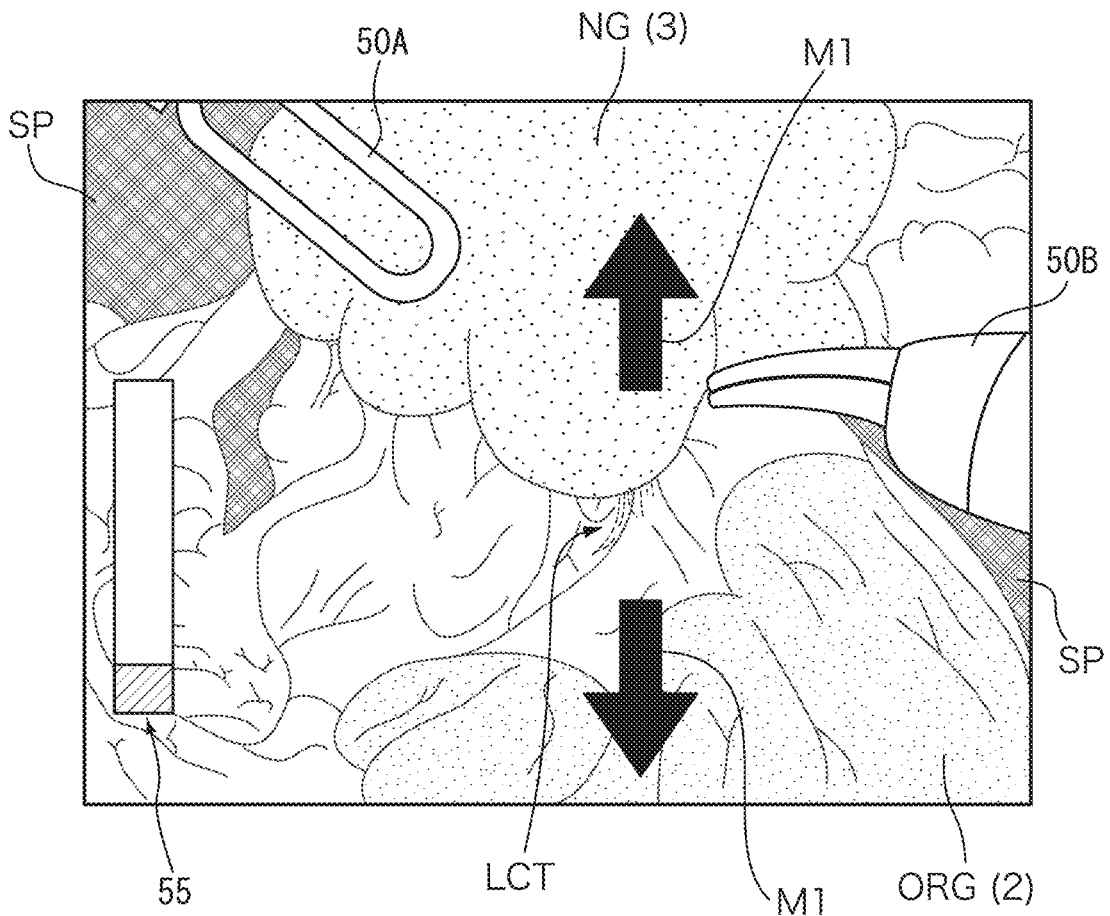
FIG. 20 is a view illustrating an output example of navigation information on the development operation.

The image processing device 30 determines a development direction of the loose connective tissue LCT from a direction in which the loose connective tissue LCT extends. For example, in the example in FIG. 19, the image processing device 30 can estimate that the loose connective tissue LCT extends in an upper and lower direction in the drawing from a recognition result of the learning model 410. Since the resection organ 3 exists on an upper side of the loose connective tissue LCT, and the preservation organ 2 exists on a lower side thereof, when the resection organ 3 is tracked to an upward side by the forceps 50A, or when the preservation organ 2 is tracked to a downward side by the forceps 50A, the loose connective tissue LCT can be developed. The image processing device 30 outputs the development direction of the loose connective tissue LCT as the navigation information. FIG. 20 is a view illustrating an output example of the navigation information on the development operation. FIG. 20 illustrates the development direction (that is, an operation direction of the forceps 50A) of the loose connective tissue LCT by an arrow mark M1.

Figure 21:
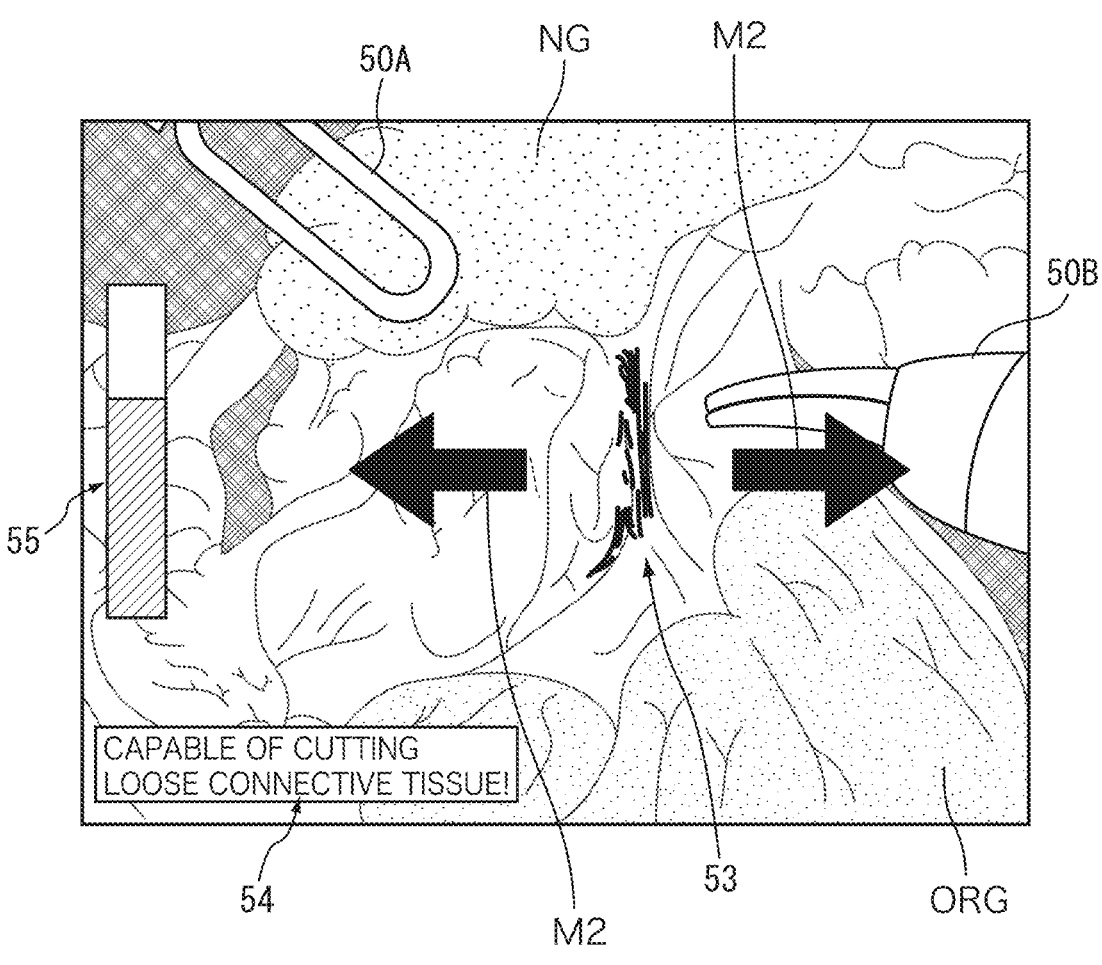
FIG. 21 is a view illustrating an output example of navigation information on a cutting operation.

On the other hand, in a case where the loose connective tissue LCT is sufficiently developed, the image processing device 30 outputs the cutting direction of the loose connective tissue LCT as the navigation information. For example, in the example illustrated in FIG. 13 or FIG. 18, since the image processing device 30 can estimate that the loose connective tissue LCT is sufficiently developed in an upper and lower direction from the recognition result by the learning model 410, the image processing device 30 determines that the cutting direction of the loose connective tissue LCT is a right and left direction in the drawing. The image processing device 30 outputs the cutting direction of the loose connective tissue LCT as the navigation direction. FIG. 21 is a view illustrating an output example of the navigation information on a cutting operation. FIG. 21 illustrates the cutting direction of the loose connective tissue LCT (that is, an operation direction of the energy treatment tool 50B) by an arrow mark M2.

In FIG. 20 and FIG. 21, the marks M1 and M2 are displayed in a relatively large size to emphasize the development direction and the cutting direction. However, in a case where a part of the operation field is hidden by the marks M1 and M2, the surgical operation may be difficult, and thus a display aspect (a size, a color, display timing, and the like) of the marks M1 and M2 may be set in order for a doctor to secure a visual field. In addition, the development direction and the cutting direction may be shown by a solid line or a broken line without limitation to the arrow marks M1 and M2. In addition, in this embodiment, the marks M1 and M2 are displayed in a manner of being superimposed on the operation field image, but the marks may be displayed in separate images or may be displayed on an additional monitor. In addition, the CPU 301 may give a notification of the development direction and the cutting direction by a voice through a microphone provided in the output device 306, and in a case where a vibrator is mounted to the surgical operating instrument, the CPU 301 may give a notification of the cutting timing by causing the vibrator to vibrate.

Figure 22:
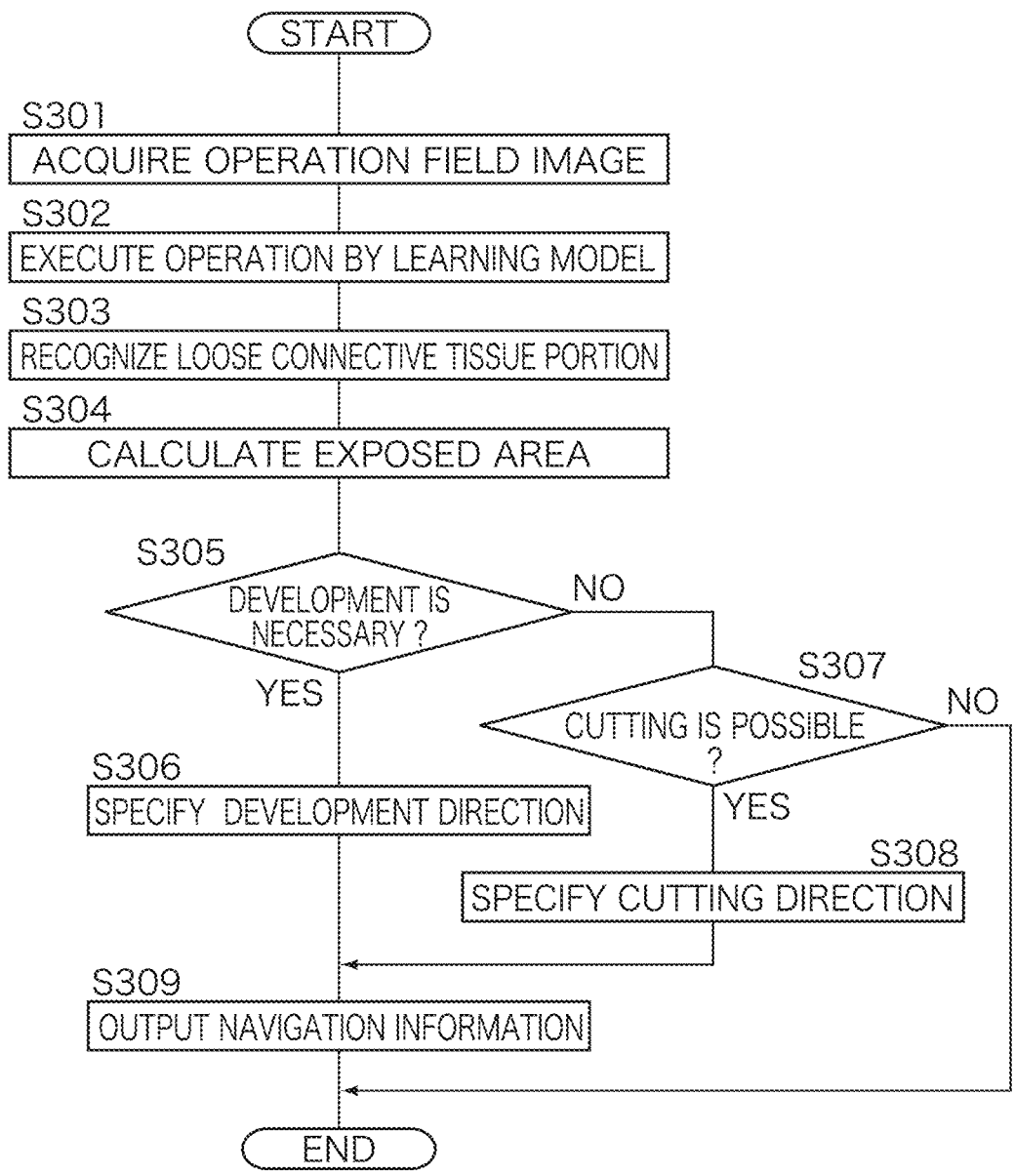
FIG. 22 is a flowchart describing a procedure that is executed in an operation phase by an image processing device according to Embodiment 3.

FIG. 22 is a flowchart illustrating a procedure that is executed in an operation phase by an image processing device 30 according to Embodiment 3. The CPU 301 of the image processing device 30 executes the following process whenever acquiring the operation field image. The CPU 301 inputs the acquired operation field image to the learning model 410 in the same procedure as in Embodiment 2, and executes an operation by the learning model 410 to recognize the loose connective tissue portion, and calculates an exposed area of the recognized loose connective tissue portion (steps S301 to S304).

The CPU 301 determines whether or not development of the loose connective tissue is necessary on the basis of the recognition result obtained by the learning model 410 (step S305). For example, the CPU 301 compares the exposed area calculated in step S304 and a first threshold value with each other, and when the calculated exposed area is less than the first threshold value, the CPU 301 determines that development of the loose connective tissue is necessary. Here, the first threshold value is set in advance and is stored in the storage device 303. In addition, the CPU 301 may determine whether or not development of the loose connective tissue is necessary by using a learning model that is trained to output information on necessity and non-necessity of development of the loose connective tissue in a case where the operation field image is input.

In a case where it is determined that development of the loose connective tissue is necessary (S305: YES), the CPU 301 specifies a development direction of the loose connective tissue (step S306). For example, the CPU 301 may estimate a direction in which the loose connective tissue between the preservation organ 2 and the resection organ 3 extends, and may specify the estimated direction as the development direction of the loose connective tissue.

In a case where it is determined that development of the loose connective tissue is not necessary (S305: NO), the CPU 301 determines whether or not cutting of the loose connective tissue is possible (step S307). For example, the CPU 301 compares the exposed area calculated in step S304 and a second threshold value with each other, and when the calculated exposed area is equal to or greater than the second threshold value, the CPU 301 determines that cutting of the loose connective tissue is possible. Here, the second threshold value is set to a value greater than the first threshold value and is stored in the storage device 303. In a case where it is determined that cutting of the loose connective tissue is not possible (S307: NO), the CPU 301 terminates the process according to this flowchart.

In a case where it is determined that cutting of the loose connective tissue is possible (S307: YES), the CPU 301 specifies the cutting direction of the loose connective tissue (step S308). For example, the CPU 301 may estimate a direction in which the loose connective tissue between the preservation organ 2 and the resection organ 3 extends, and may specify a direction intersecting the estimated direction as the cutting direction of the loose connective tissue.

Here, the CPU 301 outputs the navigation information at the time of treating the loose connective tissue between the preservation organ 2 and the resection organ 3 (step S309). For example, in a case where the development direction of the loose connective tissue is specified in step S306, the CPU 301 displays the mark M1 indicating the development direction in a manner of being superimposed on the operation field image to output the navigation information. In addition, in a case where the cutting direction of the loose connective tissue is specified in step S308, the CPU 301 displays the mark M2 indicating the cutting direction in a manner of being superimposed on the operation field image to output the navigation information.

As described above, in Embodiment 3, the development direction and the cutting direction of the loose connective tissue may be presented to a doctor as the navigation information.

Embodiment 4

In Embodiment 4, description will be given of a configuration of learning cutting timing of the loose connective tissue.

Figure 23:
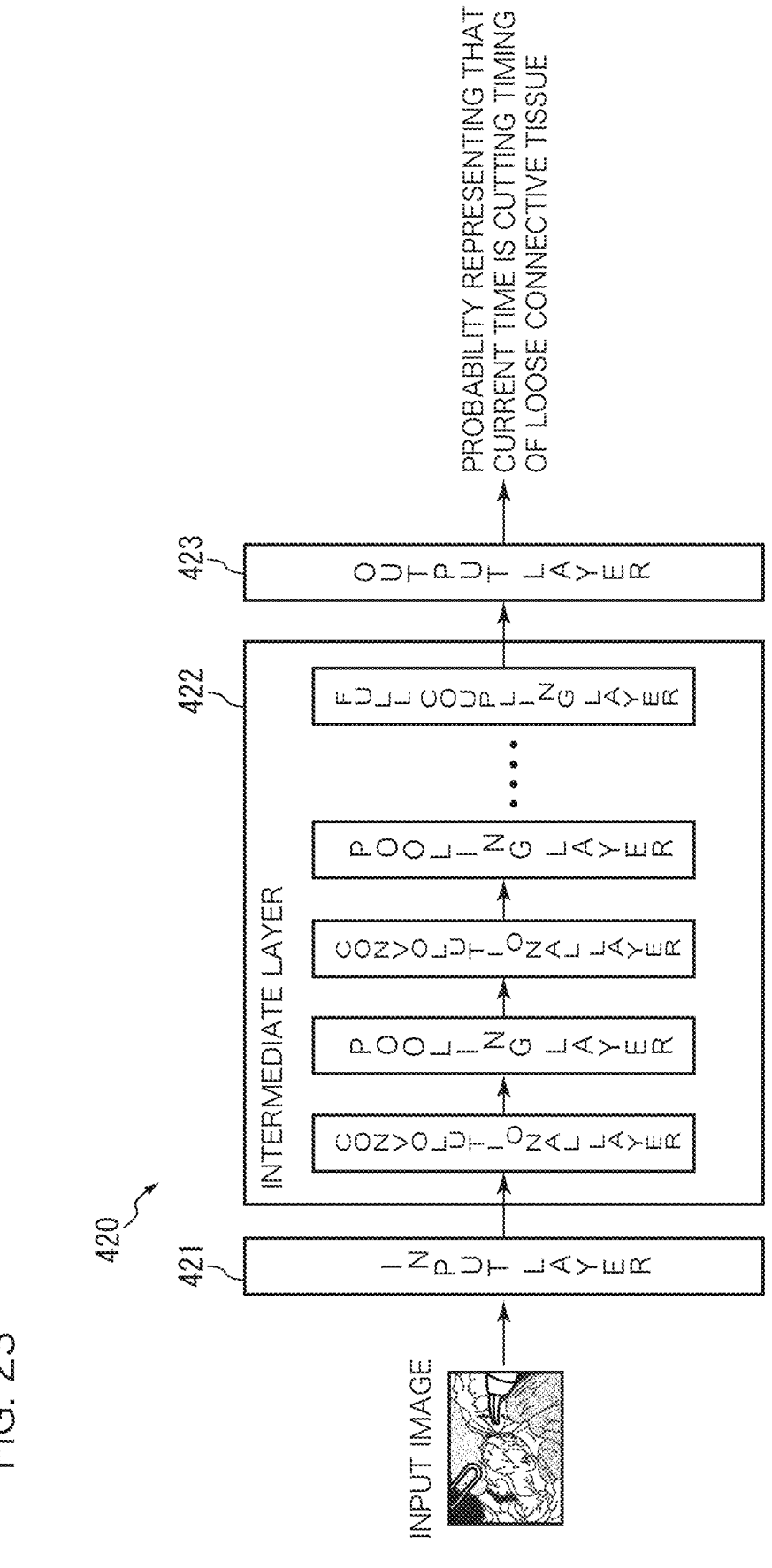
FIG. 23 is a schematic view describing a configuration of a learning model according to Embodiment 4.

FIG. 23 is a schematic view illustrating a configuration of a learning model 420 in Embodiment 4. The learning model 420 is a learning model by a convolutional neural networks (CNN), region-based CNN (R-CNN), or the like, and includes an input layer 421, an intermediate layer 422, and an output layer 423. With respect to an input of the operation field image, the learning model 420 is trained to output information on the cutting timing of the loose connective tissue. The learning model 420 is generated by the image processing device 30 or an external server that is connected to the image processing device 30 in a communication possible manner, and is stored in the model storage unit 331 of the image processing device 30.

Note that, the operation field image that is input to the learning model 420 may be a still image without limitation to a moving image. In addition, the operation field image that is input to the learning model 420 is not necessary to be a raw image obtained from the camera 21 and may be an image subjected to appropriate image processing, data representing a frequency component of an image, or the like.

The operation field image is input to the input layer 421. The intermediate layer 422 includes a convolutional layer, a pooling layer, a full coupling layer, and the like. A plurality of the convolutional layers and a plurality of the pooling layers may be alternately provided. The convolutional layer and the pooling layer extract a feature portion of the operation field image by an operation using a node of each layer. The full coupling layer couples data obtained by extracting the feature portion by the convolutional layer and the pooling layer to one node, and outputs a feature variable converted by an activation function. The feature variable is output to an output layer through the full coupling layer.

The output layer 423 includes one or a plurality of nodes. On the basis of the feature variable that is input from the full coupling layer of the intermediate layer 422, the output layer 423 performs conversion into a probability by using the soft max function, and outputs the probability after conversion from each node. In this embodiment, a probability representing that the current time is the cutting timing of the loose connective tissue may be output from the output layer 423.

The learning model 420 is generated by executing learning using an appropriate learning algorithm such as CNN and R-CNN by using a set of the operation field image, and data indicating that the loose connective tissue included in the operation field image is at the cutting timing as training data.

Figure 24:
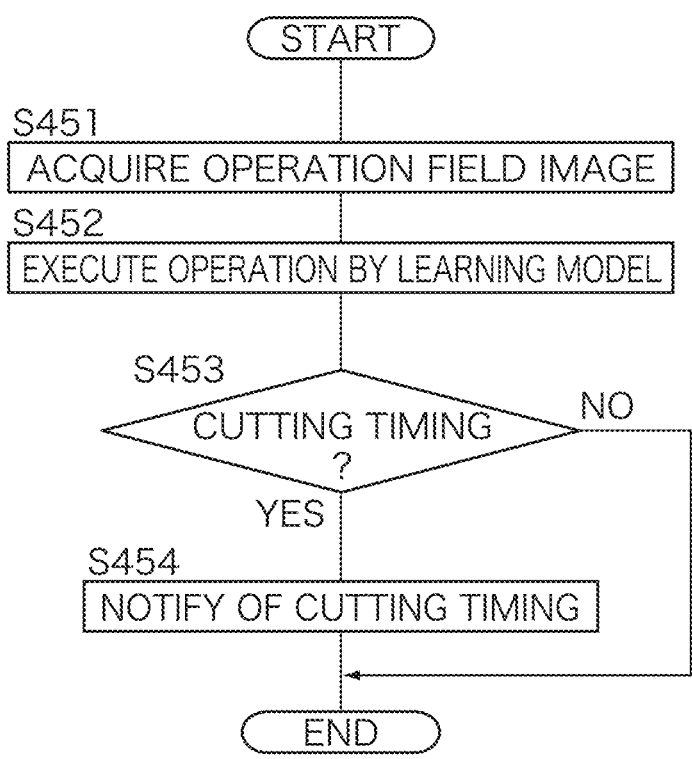
FIG. 24 is a flowchart describing a procedure that is executed in an operation phase by an image processing device according to Embodiment 4.

FIG. 24 is a flowchart illustrating a procedure that is executed in an operation phase by the image processing device 30 according to Embodiment 4. In a case of acquiring the operation field image captured by the camera 21 (step S451), the CPU 301 of the image processing device 30 inputs the acquired operation field image to the learning model 420, and executes an operation by the learning model 420 (step S452). When executing the operation using the learning model 420, a probability representing that the current time is the cutting timing of the loose connective tissue is obtained from the output layer 423.

The CPU 301 determines whether or not the current time is the cutting timing of the loose connective tissue on the basis of the probability obtained from the output layer 423 of the learning model 420 (step S453). For example, in a case where the probability output from the output layer of the learning model 420 exceeds a threshold value (for example, 50%), the CPU 301 determines that the current time is the cutting timing of the loose connective tissue, and in a case where the probability is equal to or less than the threshold value, the CPU 301 determines that the current time is not the cutting timing. In a case where it is determined that the current time is not the cutting timing (S453: NO), the CPU 301 terminates the process according to this flowchart.

In a case where it is determined that the current time is the cutting timing (S453: YES), the CPU 301 gives a notification indicating the cutting timing of the loose connective tissue (step S454). With regard to a method of giving a notification of the cutting timing, character information, an icon, a mark, or the like may be displayed in a manner of being superimposed on the operation field image, or the notification may be given with a voice or vibration as in Embodiment 2.

As described above, in Embodiment 4, the cutting timing of the loose connective tissue is determined by using the learning model 420, and the navigation information is output to perform visual assistance for a doctor with regard to the process of cutting the loose connective tissue between the tissue ORG constituting the preservation organ 2 and the tissue NG constituting the resection organ 3.

Embodiment 5

In Embodiment 5, description will be given of a configuration in which information relating to a cutting site of the loose connective tissue is output.

Figure 25:
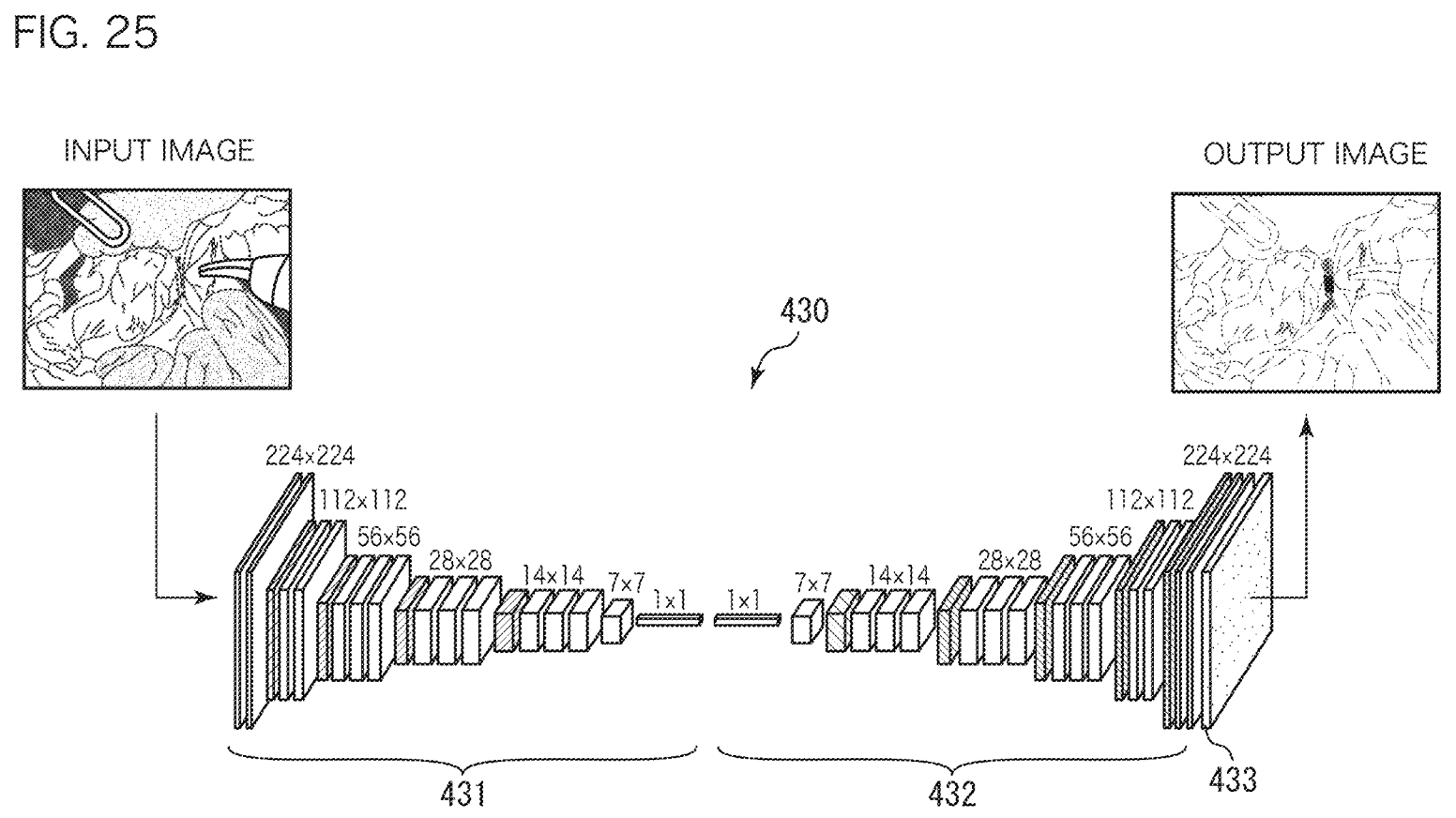

FIG. 25 is a schematic view illustrating a configuration of a learning model 430 in Embodiment 5. The learning model 430 is a learning model by a neural network for image segmentation or object detection such as SegNet, FCN, U-Net, PSPNet, YOLO, and SSD, and includes, for example, an encoder 431, a decoder 432, and a soft max layer 433. The configuration of the learning model 430 is similar to the configuration of the learning model in Embodiment 2, and thus description thereof will be omitted.

In this embodiment, an input image to the learning model 430 is an operation field image obtained from the camera 21. The operation field image that is input to the learning model 430 may a still image without limitation to a moving image. In addition, the operation field image that is input to the learning model 430 is not necessary to be a raw image obtained from the camera 21, and may be an image subjected to appropriate image processing, data representing a frequency component of an image, or the like. With respect to an input of the operation field image, the learning model 430 is trained to output an image representing a resection portion of the loose connective tissue portion included in the operation field image.

When generating the learning model 430, training data composed of a set of the operation field image and correct answer data representing a cutting site of the loose connective tissue obtained in a state of being included in the operation field image is prepared.

Figure 26:
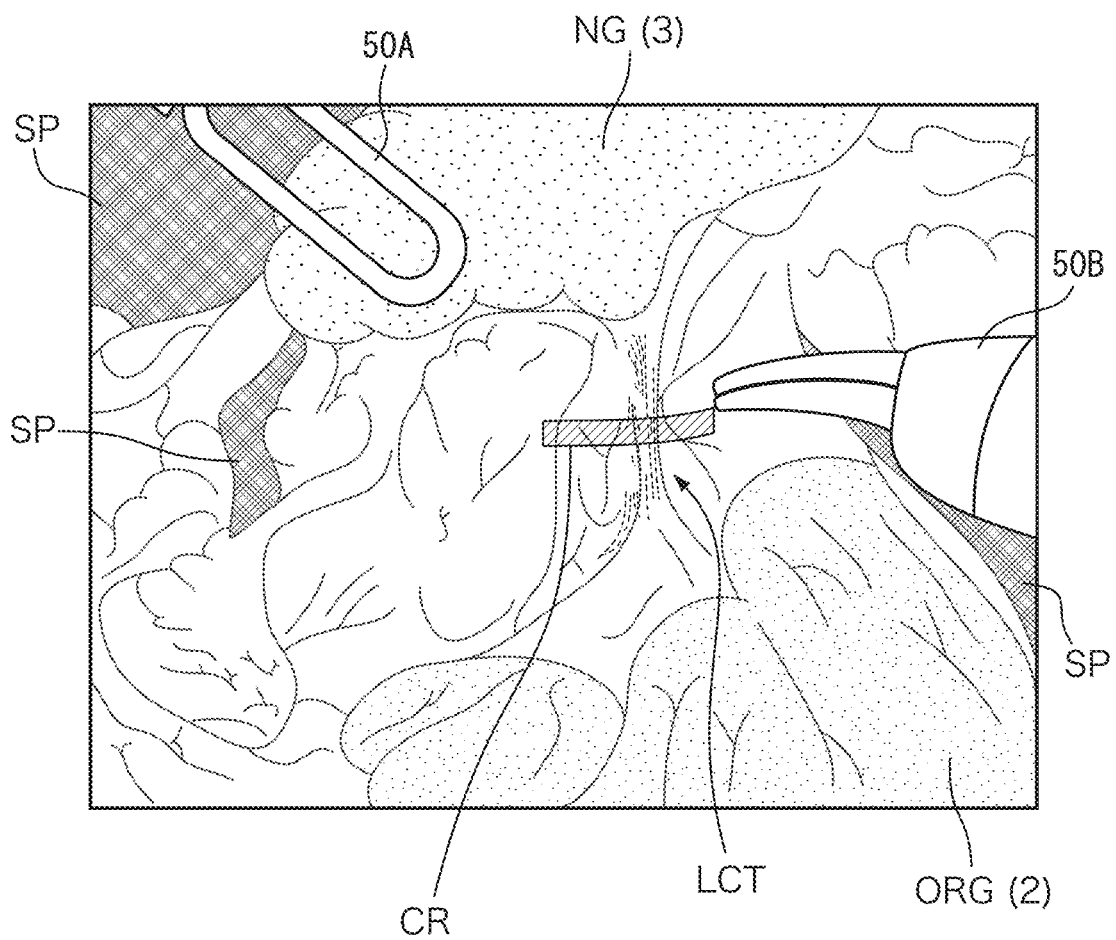
FIG. 26 is an explanatory view describing a correct answer data creation procedure.

FIG. 26 is an explanatory view illustrating a correct answer data creation procedure. A worker (a professional such as a doctor) performs annotation with respect to the operation field image including the loose connective tissue LCT. For example, the worker designates a portion corresponding to a loose connective tissue in a pixel unit in the operation field image, and designates a cutting site of the loose connective tissue LCT by a strip-shaped region CR. The image processing device 30 stores a pixel designated as the loose connective tissue LCT in the region CR in the storage device 303 as a cutting site (correct answer data) in the loose connective tissue LCT.

In addition, in a case where the learning model 410 for recognizing the loose connective tissue is obtained already, a recognition image generated by the learning model 410 may be displayed on the sub-monitor 31 in combination with the operation field image, and designation of the region CR indicating the cutting site in the displayed recognition image may be accepted.

In addition, the image processing device 30 may be configured to designate the cutting site of the loose connective tissue in the operation field image by analyzing a moving image in which the loose connective tissue is cut out by a doctor and specifying a trajectory of the surgical operation instrument 50 such as an electric knife.

The image processing device 30 generates the learning model 430 by using training data composed of a set of the operation field image and correct answer data representing the cutting site in the loose connective tissue included in the operation field image. A learning procedure is similar as in Embodiment 2, and description thereof will be omitted.

Figure 27:
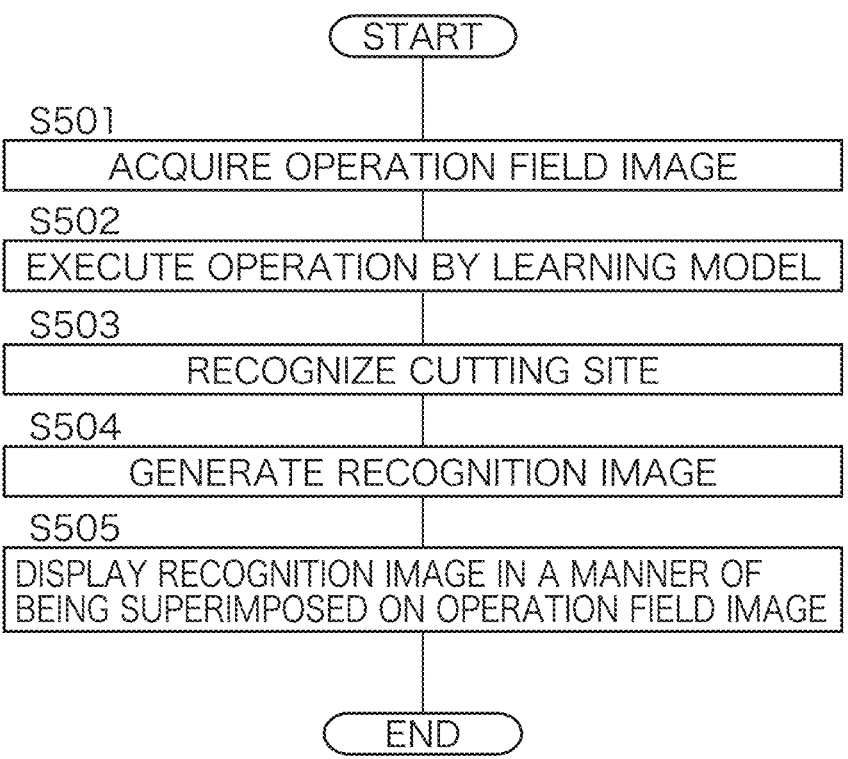
FIG. 27 is a flowchart describing a procedure that is executed in an operation phase by an image processing device according to Embodiment 5.

The image processing device 30 executes the following process in an operation phase after the trained learning model 430 is obtained. FIG. 27 is a flowchart illustrating a procedure that is executed in the operation phase by the image processing device 30 according to Embodiment 5. The CPU 301 of the image processing device 30 executes the following process whenever the operation field image is acquired. The CPU 301 inputs the operation field image that is acquired to the learning model 430 in a similar procedure as in Embodiment 2, and executes an operation by the learning model 430 to recognize a cutting site in the loose connective tissue (step S501 to S503). That is, the CPU 301 may determine whether or not each pixel corresponds to the cutting site with reference to the probability output from the soft max layer 433 of the learning model 430.

The CPU 301 generates a recognition image representing a recognition result of the recognized cutting site (step S504). The CPU 301 can generate the recognition image representing the recognition result of the cutting site by extracting pixels in which the probability of label output from the soft max layer 433 is equal to or greater than a threshold value (for example, 50% or greater). The CPU 301 may allocate a color (for example, a color of a cold color system (blue color system)) such as blue or an aqua color that does not exist inside the human body to a pixel recognized as the cutting site, and may set a transmittance to the other pixels so that the background is transmitted.

The CPU 301 displays the generated recognition image in a manner of being superimposed on the operation field image (step S505). According to this, the cutting site that is recognized by using the learning model 430 is displayed on the operation field image as a region having a specific color. In addition, the CPU 301 may display a message indicating that a region shown in a specific color is a portion to be resected on the operation field image.

Figure 28:
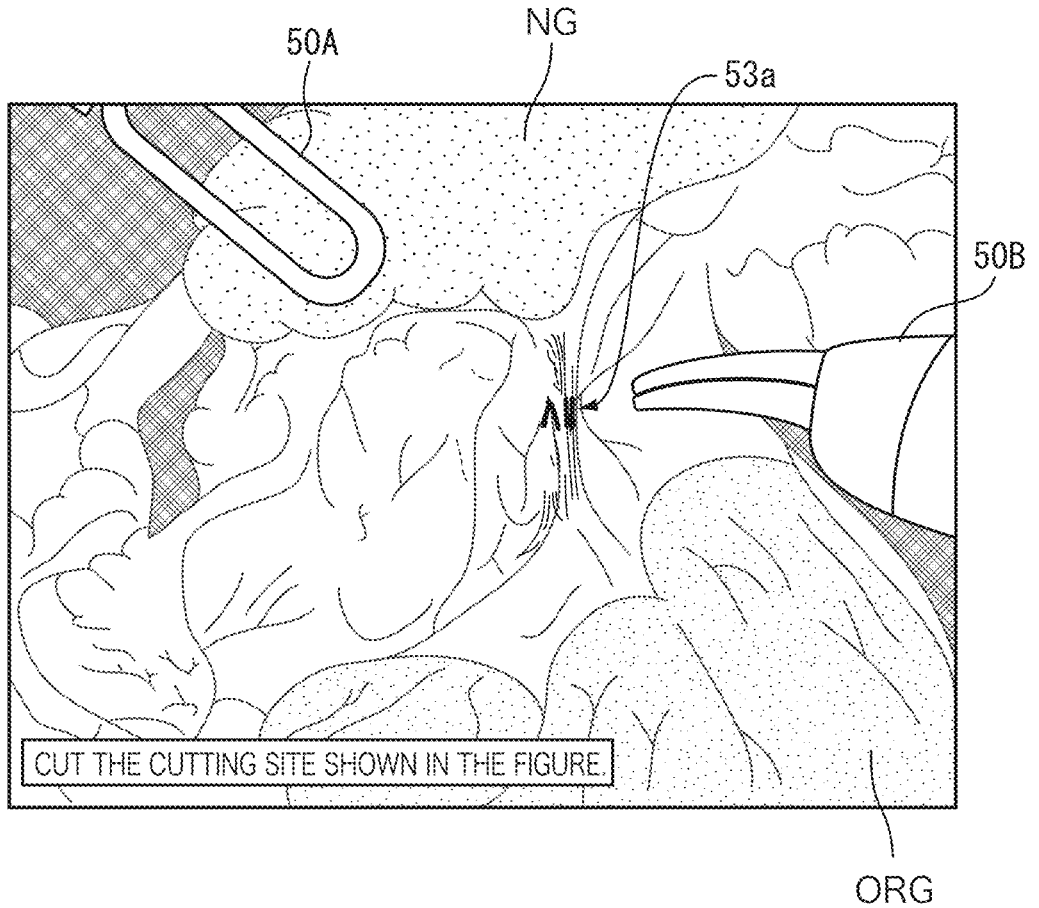
FIG. 28 is a schematic view illustrating a display example of a cutting site.

FIG. 28 is a schematic view illustrating a display example of the cutting site. For convenience of creation of the drawing, in the display example in FIG. 28, a cutting site 53*a* recognized by using the learning model 430 is shown by a bold solid-line. Actually, since a portion corresponding to the cutting site is colored in a color such as blue and aqua blue that do not exist inside the human body in a pixel unit, a doctor can clearly grasp the cutting site in the loose connective tissue when viewing a display screen of the sub-monitor 31.

As described above, in Embodiment 5, surgical operation assistance can be performed by presenting the cutting site of the loose connective tissue to the doctor.

Note that, in this embodiment, the cutting site in the loose connective tissue is recognized by using the learning model 430. However, a loose connective tissue included in an operator image and the cutting site in the loose connective tissue may be separately recognized, and a display aspect such as a color may be set to be different in such a manner that a portion recognized as the loose connective tissue is displayed, for example, in green, and a portion recognized as the cutting site in the loose connective tissue is displayed, for example, in a color such as blue. In addition, a concentration or a transparency may be changed in correspondence with a certainty factor of a recognition result (probability output from the soft max layer 433), a portion with a low certainty factor may be displayed in a light color (color with high transparency), and a portion with a high certainty factor may be displayed in a dark color (color with low transparency).

In addition, in a case where the cutting timing is recognized, the recognition image of the cutting site may be displayed in a superimposed manner in a combination of Embodiment 2 (or Embodiment 4) and Embodiment 5.

In addition, in this embodiment, a site recognized as the cutting site is colored in a pixel unit and is displayed. However, a region or a line may be generated to include a pixel recognized as the cutting site, and the generated region or line may be displayed in a manner of being superimposed on the operation field image as a recognition image of the cutting site.

Embodiment 6

In Embodiment 6, description will be given of a configuration in which an anatomical state is scored on the basis of the operation field image.

Scoring of the anatomical state represents that the quality of the anatomical state is expressed by a numerical value. In this embodiment, high and low scores are defined so that the score becomes high when the anatomical state is good, and the score becomes low when the anatomical state is bad. In a case of acquiring the operation field image captured by the camera 21, the image processing device 30 inputs the operation field image to a learning model 440 to be described later to calculate the score of the anatomical state.

Note that, the score in this embodiment 1, and a score in Embodiment 6 (and Embodiments 7 and 8 to be described later) represent a score relating to the anatomical state in combination. However, the score in Embodiment 1 represents the degree of appropriateness of the state of the connective tissue for treatment. In contrast, the score in Embodiment 6 to 8 represents the quality of the analysis result.

Figure 29:
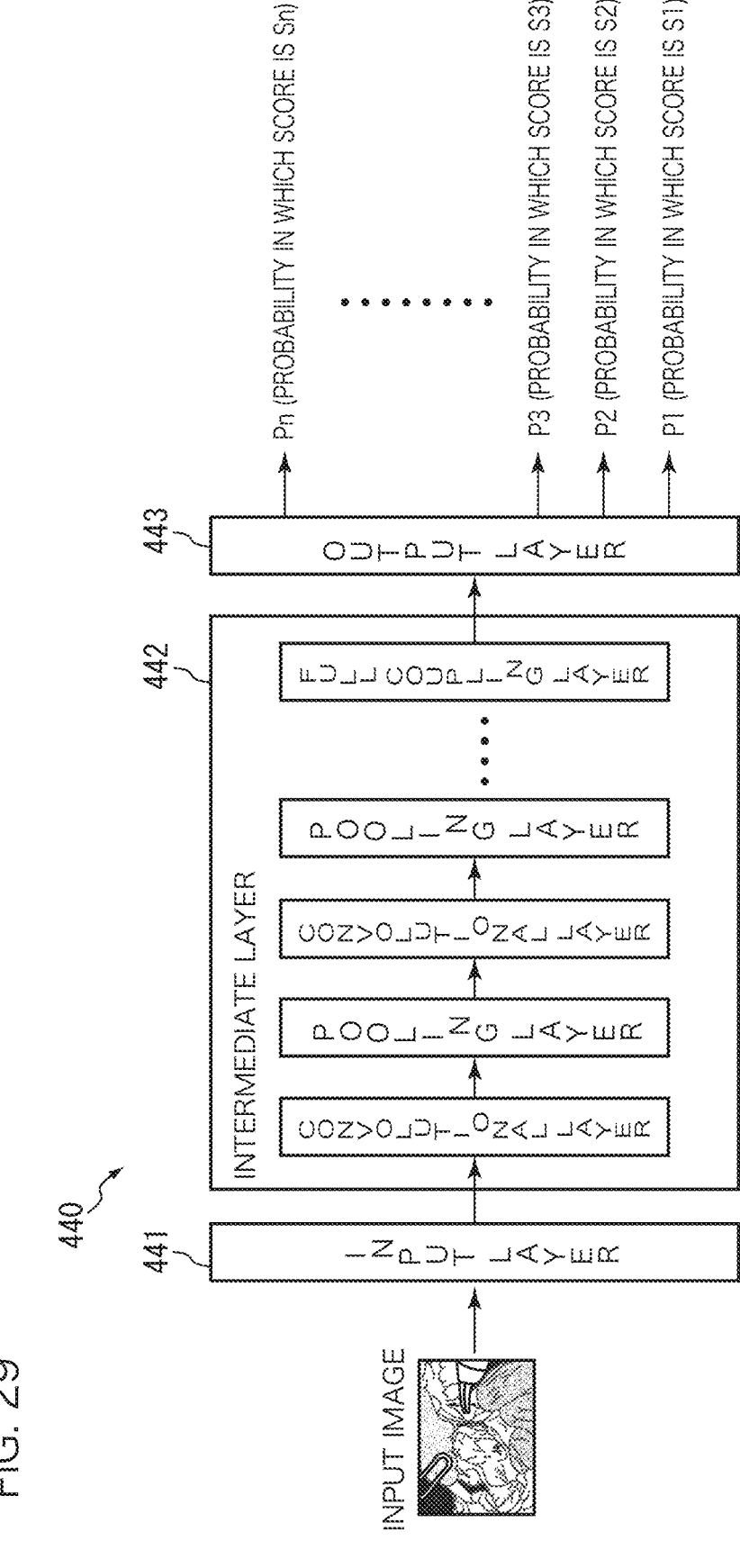
FIG. 29 is a schematic view describing a configuration of a learning model according to Embodiment 6.

FIG. 29 is a schematic view illustrating a configuration of the learning model 440 in Embodiment 6. The learning model 440 is a learning model by CNN, R-CNN, or the like, and includes an input layer 441, an intermediate layer 442, and an output layer 443. With respect to an input of the operation field image, the learning model 440 is trained to output information on the score of the anatomical state. The learning model 440 is generated by the image processing device 30 or an external server that is connected to the image processing device 30 in a communication possible manner, and is stored in the model storage unit 331 of the image processing device 30. On the other hand, the operation field image that is input to the learning model 440 may be a still image without limitation to a moving image.

Note that, the operation field image that is input to the learning model 440 is not necessary to be a raw image obtained from the camera 21, and may be an image subjected to appropriate image processing, data representing a frequency component of an image, or the like.

The operation field image is input to the input layer 441. The intermediate layer 442 includes a convolutional layer, a pooling layer, a full coupling layer, and the like. A plurality of the convolutional layers and a plurality of the pooling layers may be alternately provided. The convolutional layer and the pooling layer extract a feature portion of the operation field image by an operation using a node of each layer. The full coupling layer couples data obtained by extracting the feature portion by the convolutional layer and the pooling layer to one node, and outputs a feature variable converted by an activation function. The feature variable is output to an output layer through the full coupling layer.

The output layer 443 includes one or a plurality of nodes. On the basis of the feature variable that is input from the full coupling layer of the intermediate layer 442, the output layer 443 performs conversion into a probability by using the soft max function, and outputs the probability after conversion from each node. For example, the output layer 443 is constructed by n nodes from a first node to an nth node. A probability P1 in which the score is S1 is output from the first node, a probability P2 in which the score is S2 (>S1) is output from the second node, a probability P3 in which the score is S3 (>S2) is output from the third node, . . . , and a probability Pn in which the score is Sn (>Sn−1) is output from the nth node.

The learning model 440 illustrated in Embodiment 6 is configured to include the output layer 443 that outputs the probability of each score. However, a regressive model that is trained to calculate the score of the anatomical state in a case where the operation field image is input may be used instead of the learning model 440.

The learning model 440 is generated by executing learning on the basis of an appropriate learning algorithm by using a set of the operation field image and the score (correct answer data) determined with respect to the anatomical state in the operation field image as training data. The score of the anatomical state that is used in the training data is determined, for example, by a doctor. The doctor may confirm the anatomical state from the operation field image, and may determine the score from the viewpoints of an exposed area of the connective tissue, a tense state of the connective tissue, the number of structures such as blood vessels and adipose tissues (the degree of adhesion) existing at the periphery of the connective tissue, the degree of damage of a preservation organ, and the like. In addition, the score of the anatomical state that is used in the training data may be determined by the image processing device 30. For example, the image processing device 30 may recognize the loose connective tissue included in the operation field image by using the above-described learning model 410, may evaluate the exposed area of the loose connective tissue, the tense state, the number of structures existing at the periphery, and the like from the recognition result, and may determine the score from the evaluation result. In addition, the image processing device 30 may recognize the preservation organ, and may evaluate a color (burnt mark), a shape different from a normal shape, or the like to determine the score.

Figure 30:
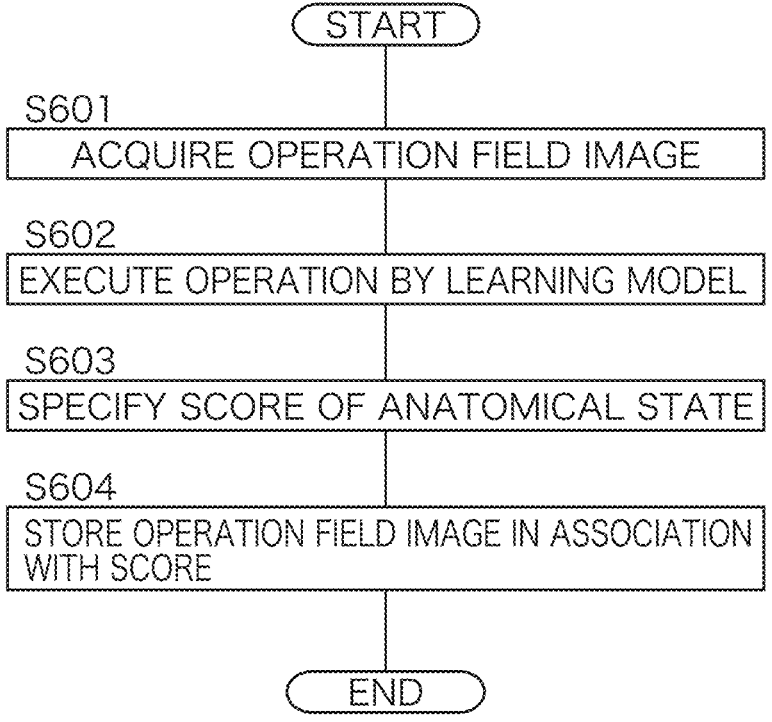
FIG. 30 is a flowchart describing a procedure that is executed by an image processing device according to Embodiment 6.

The image processing device 30 scores the anatomical state expressed by the operation field image by using the generated learning model 440. FIG. 30 is a flowchart illustrating a procedure that is executed by the image processing device 30 in Embodiment 6. In a case of acquiring an operation field image captured by the camera 21 (step S601), the CPU 301 of the image processing device 30 inputs the acquired operation field image to the learning model 440, and executes an operation by the learning model 440 (step S602). When the operation by the learning model 440 is executed, the probability for each score is obtained from each node constituting the output layer 443.

The CPU 301 specifies the score of the anatomical state with reference to an output of the learning model 440 (step S603). Since the probability with respect to each score is obtained from each node of the output layer 443, the CPU 301 may specify the score of the anatomical state by selecting a score with the highest probability.

The CPU 301 stores the operation field image in the storage device 303 in association with the specified score (step S604). At this time, the CPU 301 may store all operation field images in the storage device 303 in association with the score. In addition, the CPU 301 may extract only an operation field image in which the score is greater than a predetermined value (or smaller than the predetermined value), and may store the extracted operation field image in the storage device 303.

As described above, in Embodiment 6, the anatomical state included in the operation field image can be scored, and the operation field image and the score can be stored in the storage device 303 in association with each other. The operation field image stored in association with the score can be used for evaluation of the surgical operation, educational assistance such as training.

Embodiment 7

In Embodiment 7, description will be given of a configuration of giving an instruction for an assistant (a supporter) who assists the endoscopic surgery.

In a case where the operation field image is input, a learning model 440 in Embodiment 7 is trained to output a score relating to a state of a processing target region. For example, high and low scores are defined so that the score becomes high when the processing target region is in a state appropriate for resection, and the score becomes low when the processing target region is in a state not appropriate for resection. Here, the state appropriate for resection represents a state in which the processing target region is tracked at three points and a triangular planar portion is made. In contrast, the state not appropriate for resection represents a state in which the processing target region is not sufficiently developed, and looseness occurs.

An internal configuration of the learning model 440 is similar as in Embodiment 6, and includes an input layer 441, an intermediate layer 442, and an output layer 443. The learning model 440 is generated by executing learning on the basis of an appropriate learning algorithm by using a set of the operation field image and the score (correct answer data) determined with respect to the state of the processing target region in the operation field image as training data. The score of the processing target region that is used in the training data is determined, for example, by a doctor. The doctor may confirm the state of the processing target region from the operation field image, and may determine the score, for example, from the viewpoint of whether or not the state is appropriate for resection.

Figure 31:
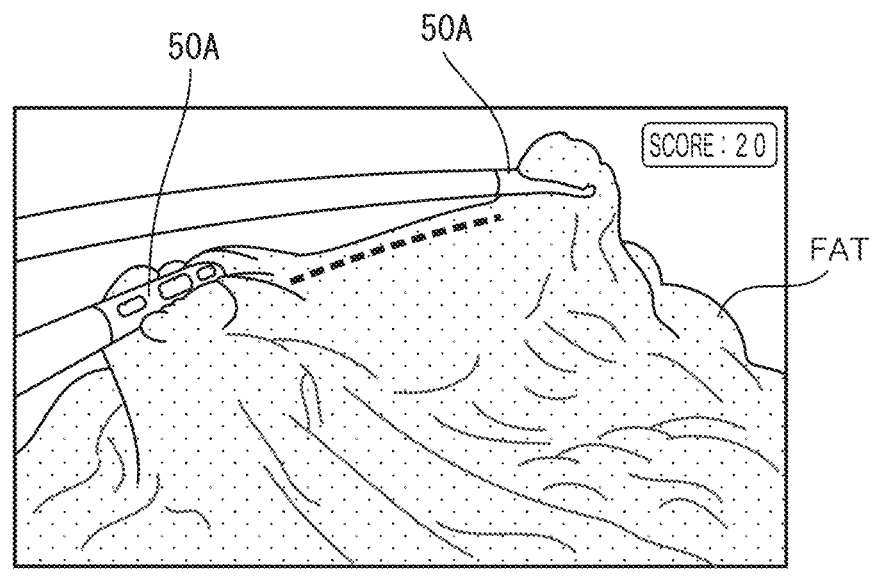
FIG. 31 is an explanatory view describing a state of a processing target region.
Figure 31:
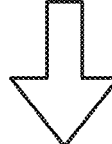
Figure 32:
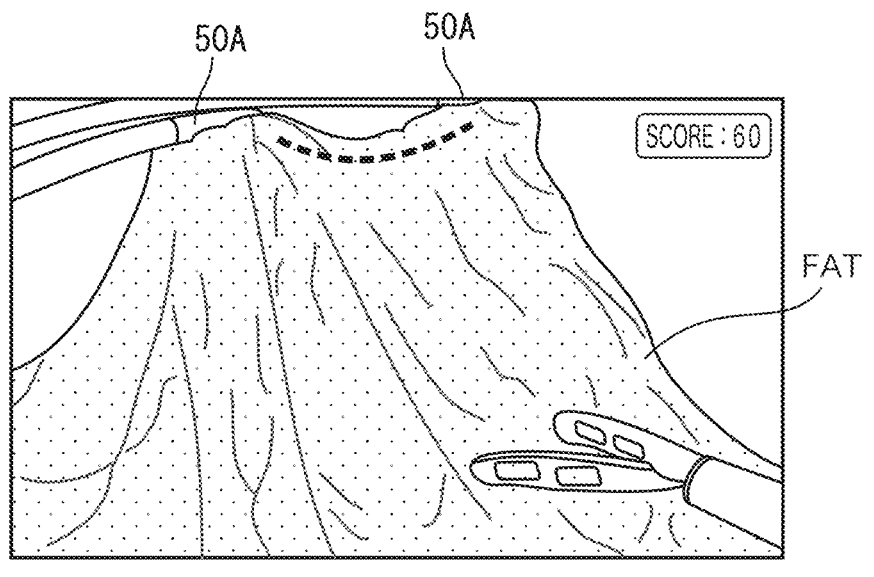
FIG. 32 is an explanatory view describing a state of a processing target region.
Figure 32:
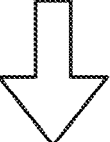
Figure 33:
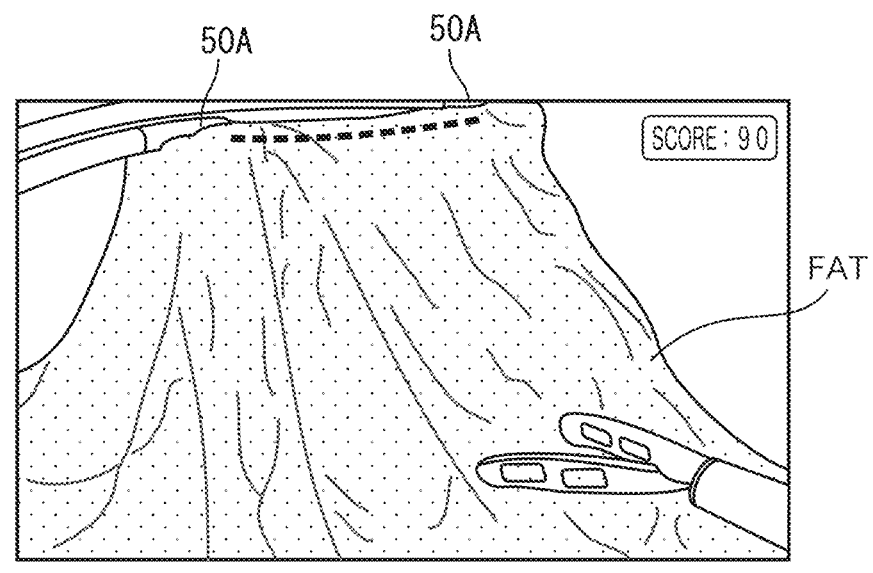
FIG. 33 is an explanatory view describing a state of a processing target region.
Figure 33:
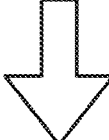

FIG. 31 to FIG. 33 is an explanatory view illustrating the state of the processing target region. FIG. 31 illustrates a state in which two different sites of an adipose tissue FAT are gripped by the forceps 50A, respectively, and the adipose tissue FAT is slightly lifted up. In this example, since the processing target region is not sufficiently developed, and looseness occurs, the processing target region is in a state in which resection is difficult. A score obtained in a case of inputting the operation field image as illustrated in FIG. 31 to the learning model 440 is relatively low, and thus the image processing device 30 performs operating assistance for an assistant so that the score is improved. For example, the image processing device 30 performs the operating assistance by giving an instruction for the assistant to develop the processing target region and remove looseness. The instruction to the assistant is performed with display on the sub-monitor 31, a voice output, or the like.

FIG. 32 illustrates a state in which two different sites of the adipose tissue FAT are gripped by the forceps 50A, respectively, and the adipose tissue FAT is sufficiently lifted up. However, an interval between the two forceps 50A is narrow, and looseness occurs therebetween. In a case of inputting an operation field image as illustrated in FIG. 32 to the learning model 440, the score is improved, but the score is not sufficient for resection. Accordingly, the image processing device 30 performs operating assistance to an assistant so that the score is further improved. For example, the image processing device 30 performs the operating assistance by giving an instruction for the assistant to develop the processing target region and remove looseness. The instruction to the assistant is performed with display on the sub-monitor 31, a voice output, or the like.

In addition, the image processing device 30 may evaluate a state of the processing target region and may give an instruction for the assistant on the basis of an evaluation result. For example, the image processing device 30 may evaluate a ridge that is formed when gripping the adipose tissue FAT at two sites. In FIG. 31 and FIG. 32, the ridge is indicated by a broken line. The ridge shown in FIG. 31 has a straight line shape, and thus looseness in a right and left direction is small, but a lift-up amount is not sufficient (a distance between the ridge and an organ is short), and thus looseness occurs in an upper and lower direction. Therefore, the image processing device 30 may give an instruction for the assistant to lift up the adipose tissue FAT by the forceps 50A. In FIG. 32, the lift-up amount is sufficient, but the ridge has an arc shape, and thus looseness occurs in a right and left direction. Therefore, the image processing device 30 may give an instruction for the assistant to broaden the adipose tissue FAT in the right and left direction by the forceps 50A.

FIG. 33 illustrates a state in which two different sites of the adipose tissue FAT are gripped by the forceps 50A, respectively, and the adipose tissue FAT is sufficiently lifted up and is broadened in a right and left direction. In a case of inputting the operation field image to the learning model 440, since the score is sufficiently improved and it is in a state suitable for resection, the image processing device 30 performs operating assistance to a doctor. The image processing device 30 performs the operating assistance by giving an instruction for the doctor to resect the processing target region. The instruction for the doctor is performed with display on the sub-monitor 31, a voice output, or the like.

As described above, in Embodiment 7, the state of the processing target region is grasped by the learning model 440, and the operating assistance to the doctor or the assistant can be performed on the basis of the grasped state of the processing target region.

Embodiment 8

In Embodiment 8, description will be given of a configuration in which a prediction image of the operation field image is generated, and the generated prediction image is output as navigation information.

Figure 34:
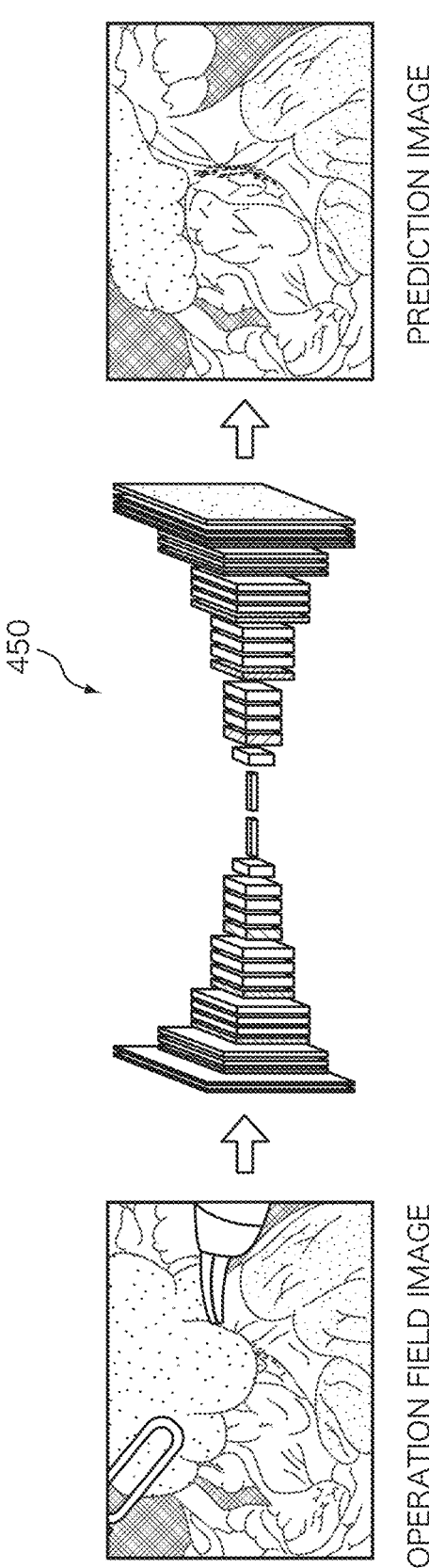
FIG. 34 is an explanatory view describing a learning model according to Embodiment 8.

FIG. 34 is an explanatory view illustrating a learning model in Embodiment 8. Embodiment 8 uses an image generation model that generates an operation field image (prediction image) configured to slightly improve the score with respect to an input of the operation field image.

For example, a learning model 450 is an image generation model that is trained to output a prediction image in which a score region is 10 to 20 in a case of inputting an operation field image in which the score region is 0 to 10 (equal to or greater than 0 and less than 10). As the image generation model, a generative adversarial network (GAN), a variational autoencoder (VAE), an autoencoder, a flow base generation model, or the like can be used. For example, the learning model 450 is generated by reading out an operation field image (input data) in which the score region is 0 to 10 and an operation field image (correct answer data) in which the score region is 10 to 20 from the storage device 303, and by performing learning by using the set as training data.

Similarly, an image generation model that generates an operation field image so that the score is slightly improved with respect to an input of the operation field image is prepared in advance. Examples of the image generation model include a learning model that is trained to output a prediction image in which the score region is 20 to 30 in a case of inputting an operation field image in which the score region is 10 to 20, a learning model that is trained to output a prediction image in which the score region is 30 to 40 in a case of inputting an operation field image in which the score region is 20 to 30, . . . , and the like.

Note that, the operation field image that is input to the image generation model may be a still image without limitation to a moving image. In addition, the operation field image that is input to the image generation model is not necessary to be a raw image obtained from the camera 21, and may be an image subjected to appropriate image processing, data representing a frequency component of an image, or the like. In addition, the score region of the operation field image that is input to the image generation model, and the score region of the operation field image that is output from the image generation model can be appropriately set without limitation to the above-described ranges. In addition, in this embodiment, an actually captured operation field image is used as the correct answer data in the learning, but as the correct answer data, a virtual operation field image drawn by 3D graphics may be used.

Figure 35:
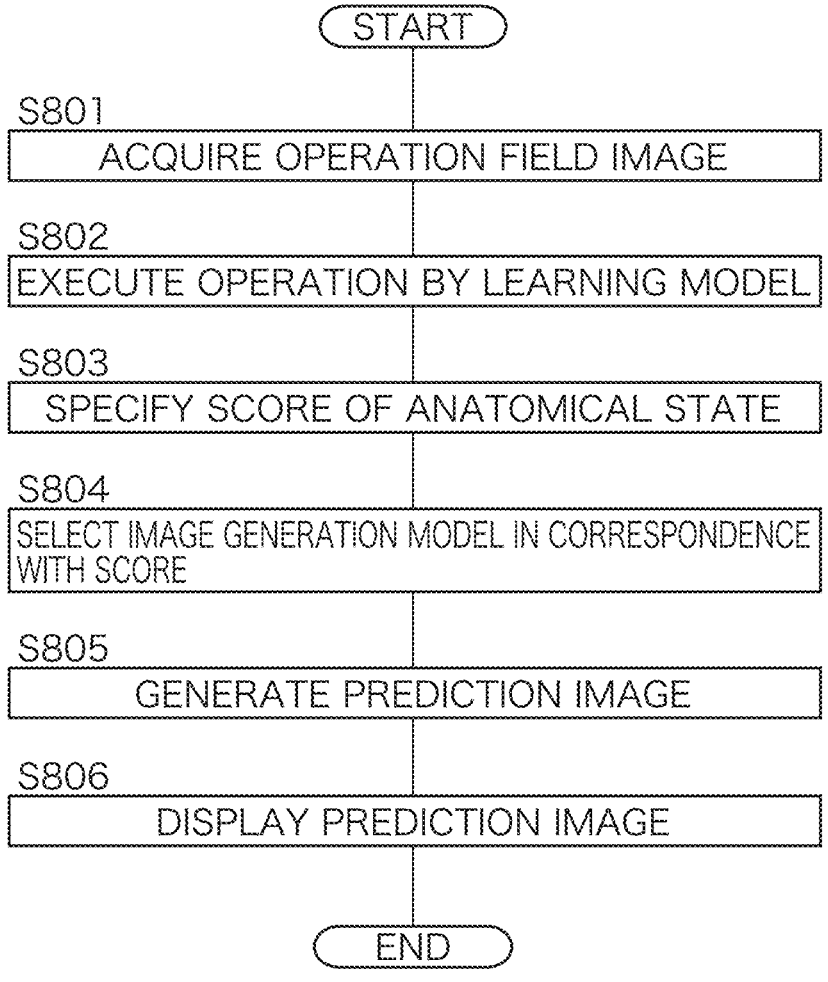
FIG. 35 is a flowchart describing a procedure that is executed by an image processing device according to Embodiment 8.

In an operation phase after the image generation model is generated, the image processing device 30 generates the prediction image by using the image generation model and presents the prediction image to a doctor. FIG. 35 is a flowchart illustrating a procedure that is executed by the image processing device 30 in Embodiment 8. In a case of acquiring an operation field image captured by the camera 21 (step S801), the CPU 301 of the image processing device 30 inputs the acquired operation field image to the learning model 440 described in Embodiment 6, and executes an operation by the learning model 440 (step S802). When the operation by the learning model 440 is executed, the probability with respect to each score is obtained from each node constituting the output layer 443.

The CPU 301 specifies the score of the anatomical state with reference to an output of the learning model 440 (step S803). Since the probability with respect to each score is obtained from each node constituting the output layer 443, the CPU 301 may specify the score of the anatomical state by selecting a score with the highest probability.

The CPU 301 selects an image generation model in correspondence with the specified score (step S804). For example, when the score specified in step S803 is a score region of 0 to 10, the CPU 301 selects the learning model 450. This is also true of a case where the score specified in step S803 is a different score region, and the CPU 30 may select a learning model that is prepared with respect to each score region.

The CPU 301 inputs the operation field image to the selected image generation model, and executes an operation by the image generation model to generate the prediction image (step S805). The CPU 301 displays the generated prediction image on the sub-monitor 31 (step S806). At this time, the CPU 301 may display the prediction image separately from the operation field image.

As described above, in Embodiment 8, the prediction image of the anatomical state can be displayed, operating assistance for a doctor can be executed.

Hereinbefore, the embodiments have been described, but the above-described embodiments are given for easy understanding of the invention, and are not intended to limit interpretation of the invention. The invention can be modified and improved without departing from the spirit of the invention, and an equivalent thereof is also included in the invention.

It is noted that, as used herein and in the appended claims, the singular forms "a", "an", and "the" include plural referents unless the context clearly dictates otherwise.

The invention claimed is:

1. A non-transitory recording medium recoding a program that causes a computer to execute processing comprising:
   acquiring an operation field image obtained by imaging an operation field of an endoscopic surgery;
   inputting the acquired operation field image to a learning model trained to output a recognition result of a connective tissue between a preservation organ and a resection organ where there is a space behind the connective tissue, in a case where the operation field image is input, and recognizing the connective tissue included in the operation field image;
   calculating an exposed area of the connective tissue that is exposed as a result of the resection organ being pulled away from the preservation organ, and that is recognized by the learning model; and
   outputting an indicator representing a magnitude of the calculated exposed area as navigation information when treating the connective tissue between the preservation organ and the resection organ.

2. The non-transitory recording medium according to claim 1,
   wherein the computer is caused to execute processes of,
   determining if the connective tissue can be cut on the basis of the calculated exposed area, and
   outputting information whether the connective tissue can be cut as the navigation information.

3. The non-transitory recording medium according to claim 1,
   wherein the computer is caused to execute processes of,
   determining an operating direction of an operation tool when developing or cutting the connective tissue on the basis of the recognition result that is output from the learning model, and
   outputting information on the determined operating direction as the navigation information.

4. The non-transitory recording medium according to claim 1,
   wherein the resection organ being pulled away from the preservation organ causes tension on the connective tissue thereby putting the connective tissue in a tense state,
   wherein the learning model is trained to recognize a connective tissue that is in a tense state in a case where the operation field image is input, and
   the computer is caused to execute processes of,
   outputting information indicating that cutting the connective tissue is appropriate as the navigation information, in a case where the connective tissue that is in the tense state is recognized by the learning model.

5. The non-transitory recording medium according to claim 1, wherein the learning model is trained to output information on if the connective tissue between the preservation organ and the resection organ can be cut in a case where the operation field image is input, and the computer is caused to execute a process of outputting whether the connective tissue can be cut that is obtained from the learning model as the navigation information.

6. The non-transitory recording medium according to claim 1, wherein the learning model is trained to output information on a cutting site in the connective tissue between the preservation organ and the resection organ in a case where the operation field image is input, and the computer is caused to execute a process of outputting the information on the cutting site which is obtained from the learning model as the navigation information.

7. The non-transitory recording medium according to claim 1, wherein the learning model is trained to output a score relating to an anatomical state in a case where the operation field image is input.

8. The non-transitory recording medium according to claim 7, wherein the learning model is trained so that the score fluctuates in accordance with at least any one among an exposed area of the connective tissue, a tense state of the connective tissue, the number of structures existing at the periphery of the connective tissue, and the degree of a damage of the preservation organ, wherein a tense state of the connective tissue is caused by the resection organ being pulled away from the preservation organ causing tension on the connective tissue.

9. The non-transitory recording medium according to claim 7, wherein the computer is caused to execute a process of storing the operation field image that is input to the learning model, and the score obtained by inputting the operation field image to the learning model in a storage device in association with each other.

10. The non-transitory recording medium according to claim 7, wherein the learning model is trained so that the score fluctuates in accordance with a state of a processing target region, and the computer is caused to execute a process of outputting an instruction to an assistor who assists the endoscopic surgery on the basis of the score that is output from the learning model.

11. The non-transitory recording medium according to claim 1, wherein the computer is caused to execute processes of, inputting the acquired operation field image to an image generation model that is trained to generate a prediction image of an anatomical state in a case where the operation field image is input, and acquiring a prediction image with respect to the operation field image, and outputting the acquired prediction image as the navigation information.

12. A non-transitory recording medium recoding a program that causes a computer to execute processing comprising:

acquiring an operation field image obtained by imaging an operation field of an endoscopic surgery;

inputting the acquired operation field image to a learning model trained to recognize a connective tissue between a preservation organ and a resection organ by distinguishing between connective tissue under tension and connective tissue not under tension in a case where the operation field image is input, and acquiring information on the connective tissue included in the operation field image, wherein connective tissue under tension occurs when the resection organ is pulled away from the preservation organ, and wherein connective tissue not under tension occurs when the resection organ is not pulled away from the preservation organ; and displaying textual information on a display screen indicating that connective tissue can be cut on the basis of a calculated exposed area, when recognizing the connective tissue under tension based on an acquired information from the learning model.

* * * * *